(12) United States Patent
Wang et al.

(10) Patent No.: US 8,513,227 B2
(45) Date of Patent: Aug. 20, 2013

(54) INHIBITION OF INFLAMMATORY CYTOKINE PRODUCTION WITH TANSHINONES

(75) Inventors: Haichao Wang, Edison, NJ (US); Dazhi Chen, Jamaica Estates, NY (US); Andrew E. Sama, Manhasset, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 545 days.

(21) Appl. No.: 12/087,625

(22) PCT Filed: Jan. 12, 2007

(86) PCT No.: PCT/US2007/000945
§ 371 (c)(1), (2), (4) Date: Mar. 3, 2009

(87) PCT Pub. No.: WO2007/084419
PCT Pub. Date: Jul. 26, 2007

(65) Prior Publication Data
US 2009/0221542 A1    Sep. 3, 2009

Related U.S. Application Data

(60) Provisional application No. 60/759,237, filed on Jan. 13, 2006.

(51) Int. Cl.
*A61K 31/58* (2006.01)
*A61K 31/34* (2006.01)
*A01N 43/08* (2006.01)

(52) U.S. Cl.
USPC .......................................... 514/172; 514/468

(58) Field of Classification Search
USPC ................................. 514/172, 468
See application file for complete search history.

(56) References Cited

U.S. PATENT DOCUMENTS
2004/0039050 A1    2/2004    Gu et al.

FOREIGN PATENT DOCUMENTS

| CN | 1457851 | * | 11/2003 |
| CN | 1457851 A | | 11/2003 |
| JP | 63-267798 A | | 11/1988 |
| WO | 2005/063232 A1 | | 7/2005 |
| WO | 2007-040345 A1 | | 4/2007 |

OTHER PUBLICATIONS

Shilin (Journal of Traditional Chinese Medicine (1987) 7:131-134).*
Jang et. al. (Planta Medica (2003) 69:1057-1059).*
Takahashi et. al. (Biochemical Pharmacology (2002) 64: 745-750).*
Sharma et. al. (Expert Opinion on Investigational Drugs (2003) 12:139-152).*
Arrieta et. al. (Expert Opinion on Therapeutic Patents (2000) 10:601-622).*

The Office Action for European Application No. 07 718 166.7-1223, dated Jul. 13, 2010.
The International Search Report for PCT Application No. PCT/US2007/00945.
The Written Opinion of the International Searching Authority for PCT Application No. PCT/US2007/00945.
European Office Action dated Apr. 27, 2011, issued in corresponding European Application No. 07 718 166.7.
Chinese Office Action dated Jan. 4, 2011, issued in corresponding Chinese Applicaton No. 200780007383.3.
European Intention to Grant dated Dec. 19, 2012, issued in corresponding European Application No. 07 718 166.7.
Third Chinese Office Action dated Sep. 10, 2012 in Chinese Patent Application No. 200780007383.3.
Office Action in corresponding Australian application, "Examiner's first report on patent application No. 2007207675," dated Nov. 17, 2011.
He Shilin, et al. "Experimental Studies on the Anti-Endotoxin-Shock Effect of Radix Salviae Miltiorrhizae Compasita," Journal of Traditional Chinese Medicine, 1987, vol. 7, No. 2, p. 131-134.
Jang, et al. "Tanshinone IIA from Salvia Miltiorrhiza Inhibits Inducible Nitric Oxide Synthase Expression and Production of TNF-a, IL-1B and IL-6 in Activated RAW 264.7 Cells," Planta Medica, 2003, vol. 69, p. 1057-1059.
Japanese Preliminary Notice of Rejection dated Jul. 3, 2012 in Japanese Patent Application No. 2008-550444 with English translation.
Second Chinese Office Action dated Jan. 11, 2012, issued in corresponding Chinese Application 200780007383.3 in Chinese language and English language Translation thereof.
Communication Supplementary European Search Report, Application No. 07718166.7 dated Jun. 25, 2010, 6 pages.
Ryu, et al. "Inhibition of Mast Cell Degranulation by Tanshinones from the Roots of *Salvia miltiorrhiza*", Planta Med. 65 (1999), 654-655.
Achike, et al. "Nitric Oxide, Human Diseases and the Herbal Products That Affect the Nitric Oxide Signalling Pathway," Clin. and Exp. Pharma. and Physio. (2003) 30,605-615.
Jang, et al. "Tanshinone IIA from *Salvia miltiorrhiza* Inhibits Inducible Nitric Oxide Synthase Expression and Production of TNF-Alpha, IL-1 Beta and IL-6 in Activated RAW 264.7 Cells", Planta Med. 69 (2003) 1057-1059.
Kim, et al. "Effects of Tanshinone I Isolated from *Salvia miltiorrhiza* Bunge on Arachidonic Acid Metabolism and In Vivo Inflammatory Responses" Phytother. 16, 616 (2002).
Shulin, et al. "Experimental Studies on the Anti-Endotoxin-Shock Effect of Radix *Salviae miltiorrhizae* Composita", J. of Trade Chinese Med. 7 (2): 131-134 (1987).
Takahaski, et al. "Socium tanshinone IIA sulfonate derived from Danshen (*Salvia miltiorrhiza*) attenuates hypertrophy induced by angiotensin II in cultured neonatal rat cardiac cells", Biochem. Pharma 64 (2002) 745-750.
Wan, et al. "Protection of lethal toxicity of endotoxin by *Salvia miltiorrhiza* BUNGE is via reduction in tumor necrosis factor alpha release and liver injury", Int'l. Immunopharmacology 6 (2006) 750-758.

* cited by examiner

*Primary Examiner* — Marcos Sznaidman
(74) *Attorney, Agent, or Firm* — Amster, Rothstein & Ebenstein LLP

(57) ABSTRACT

Provided are methods of attenuating release of a proinflammatory cytokine from a mammalian cell. Also provided are methods of inhibiting or treating an inflammatory cytokine cascade in a mammal. Further provided are methods of treating a mammal at risk for or undergoing sepsis, septicemia, and/or endotoxic shock. Additionally provided are methods of attenuating NO release from a mammalian cell. Also provided are methods of attenuating NO production in a mammal at risk for, or having, a disorder mediated by excessive NO production.

8 Claims, 10 Drawing Sheets

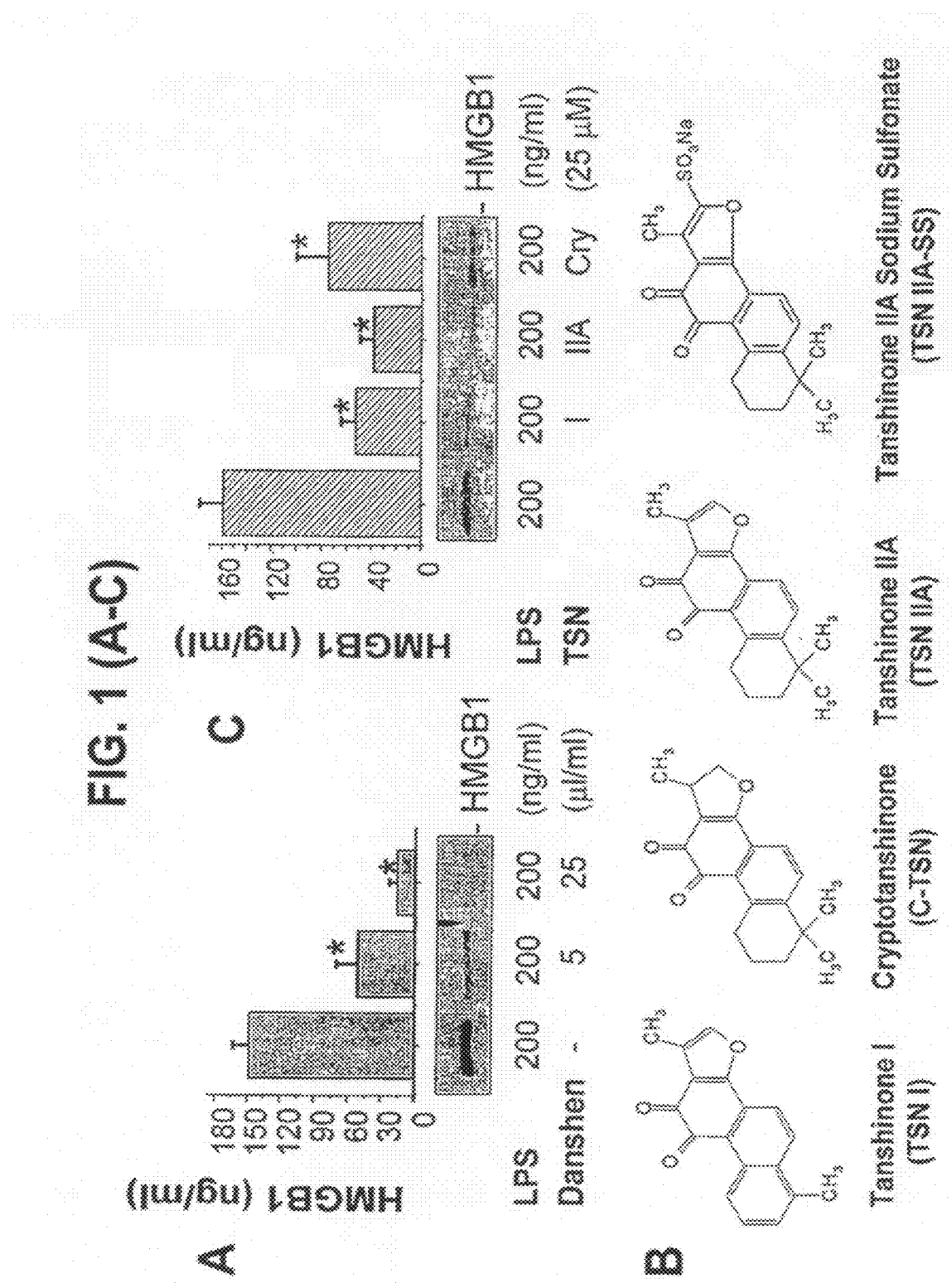
FIG. 1 (A-C)

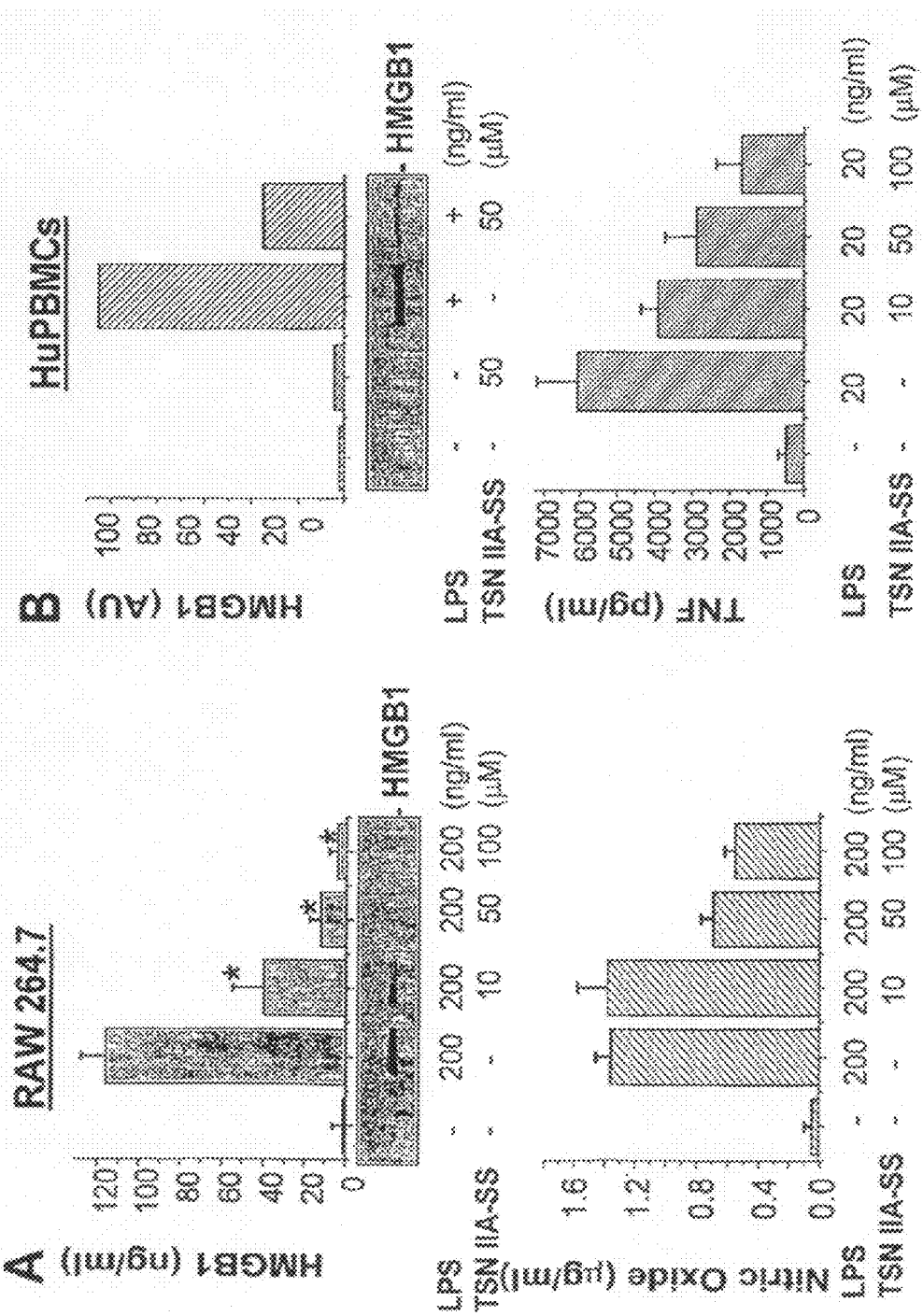
FIG. 2 (A-B)

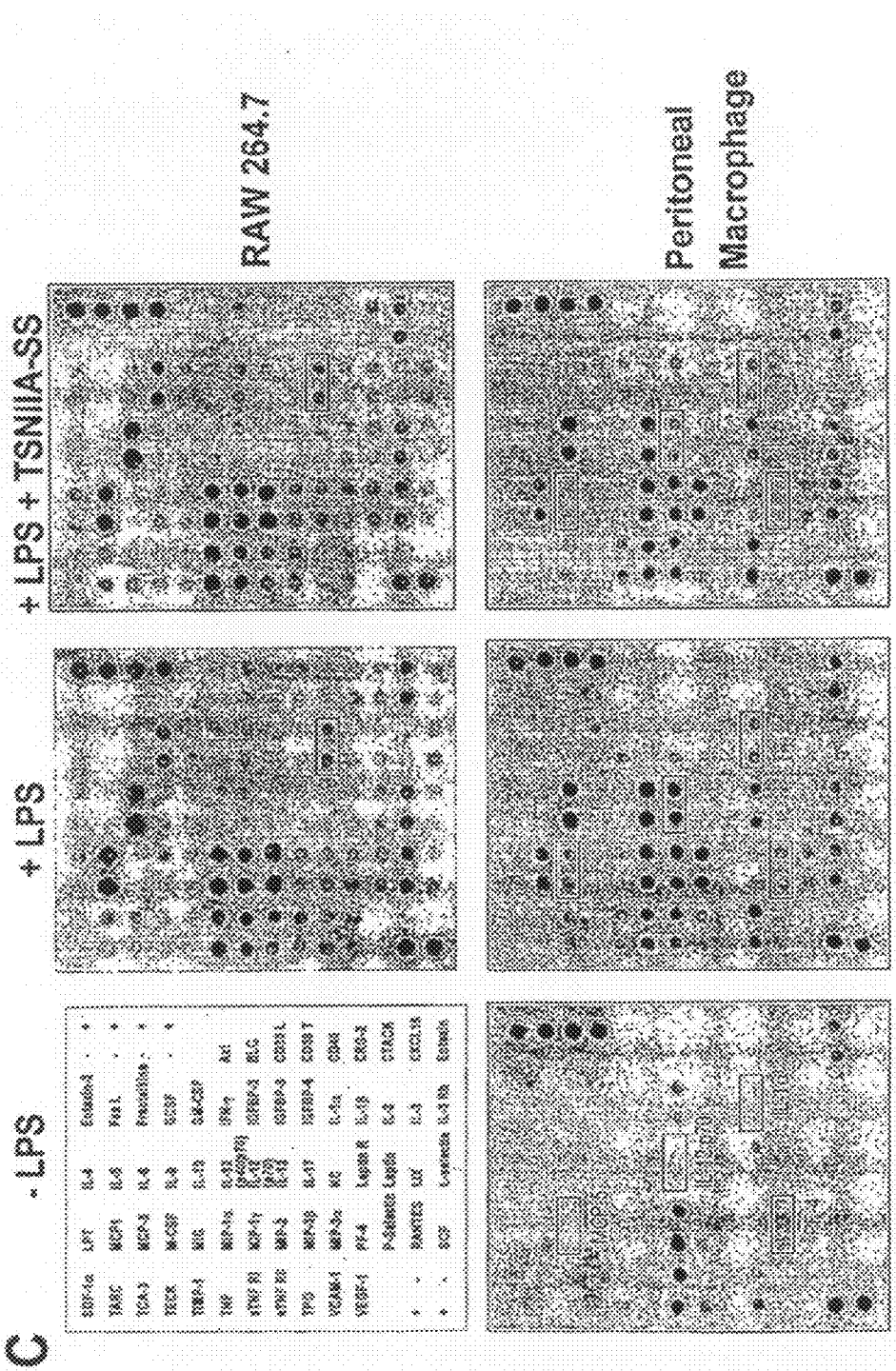

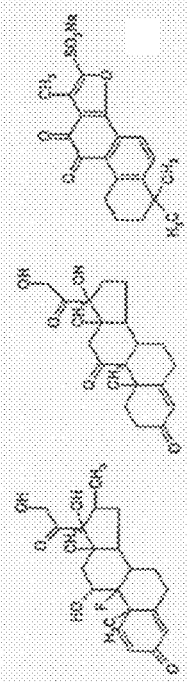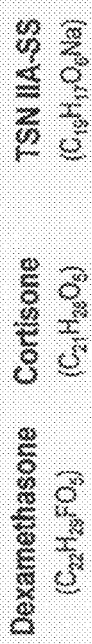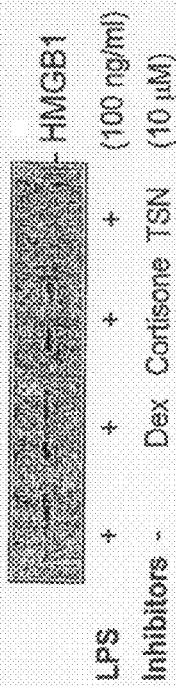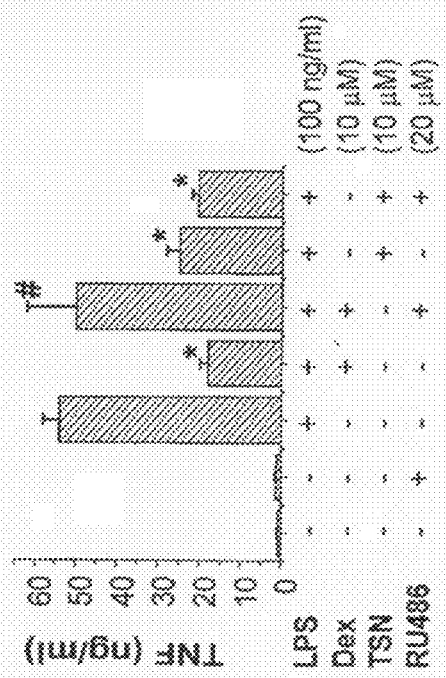
FIG. 5

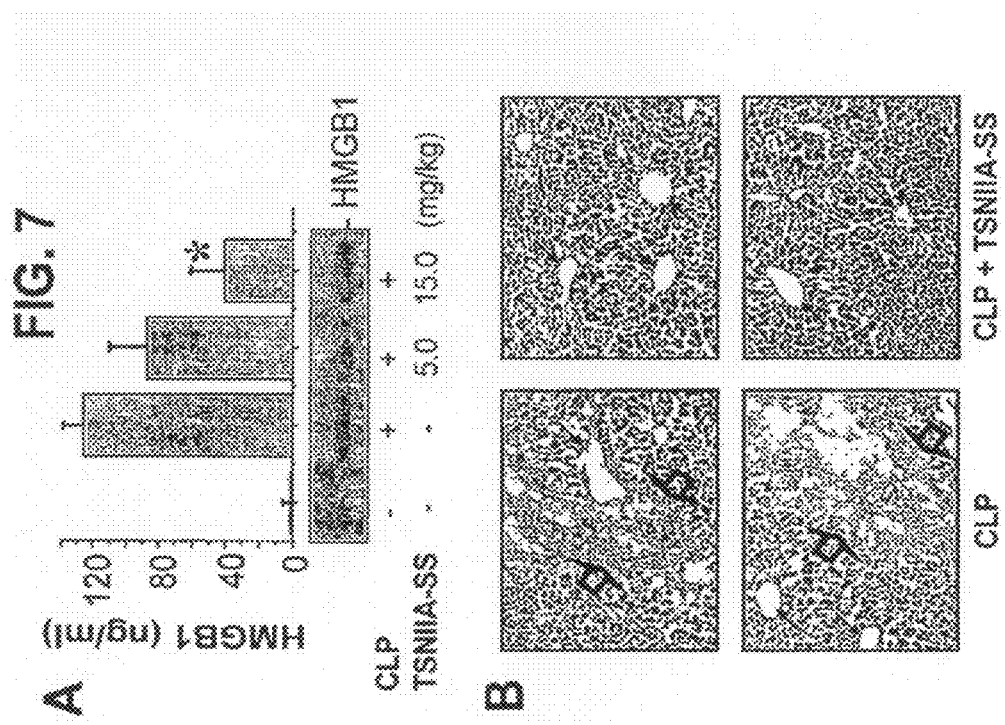

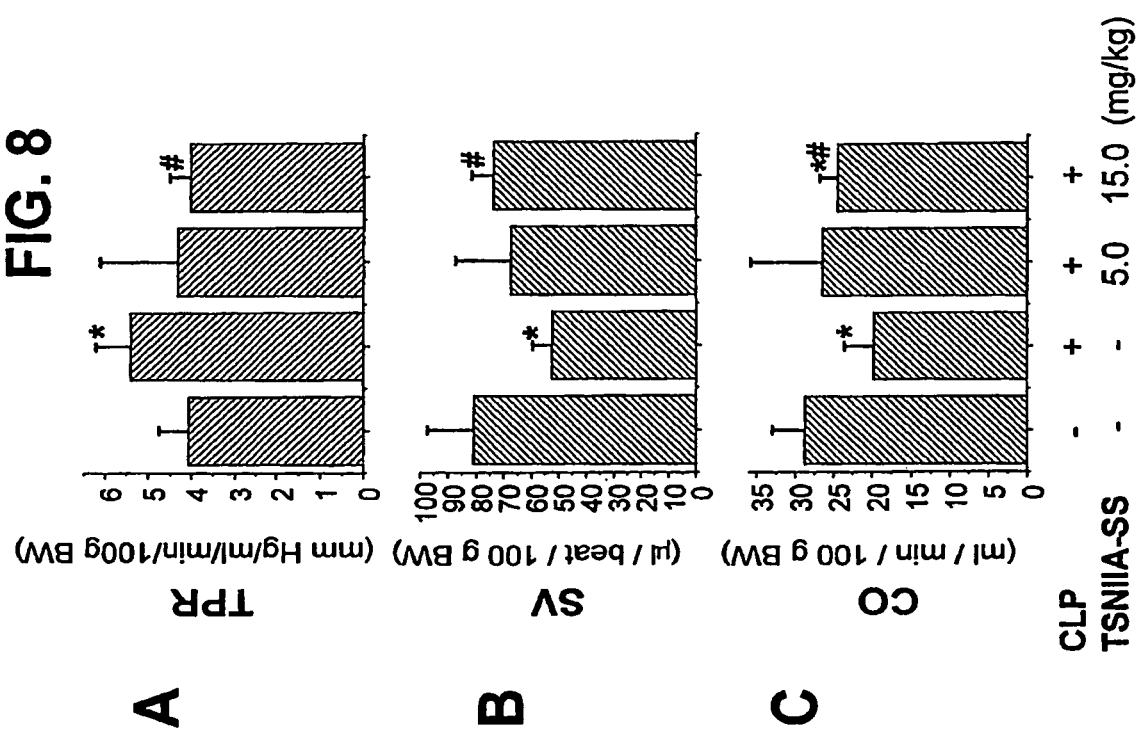

INHIBITION OF INFLAMMATORY CYTOKINE PRODUCTION WITH TANSHINONES

CROSS-REFERENCE TO RELATED APPLICATION

This is a U.S. national phase of PCT Application No. PCT/US2007/000945, filed Jan. 12, 2007, which claims the benefit of U.S. Provisional Application No. 60/759,237, filed Jan. 13, 2006.

STATEMENT REGARDING FEDERALLY SPONSORED RESEARCH OR DEVELOPMENT

The invention was made with government support under Grant Nos. R01GM063075 and R01GM070817 awarded by the National Institutes of Health. The government has certain rights in this invention.

BACKGROUND OF THE INVENTION

1. Field of the Invention

The present invention generally relates to treatments for inflammation. More specifically, the invention is directed to the use of tanshinones and tanshinone derivatives to inhibit inflammatory cytokine production.

2. Description of the Related Art

"Severe sepsis" is a syndrome defined by signs of organ dysfunction that include abnormalities in body temperature, heart rate, respiratory rate, and leukocyte counts. Despite recent advances in antibiotic therapy and intensive care, sepsis is still the most common cause of death in the intensive care units, claiming approximately 225,000 victims annually in the U.S. alone. The pathogenesis of sepsis is attributable, at least in part, to dys-regulated systemic inflammatory responses characterized by excessive accumulation of various proinflammatory mediators such as tumor necrosis factor (TNF) (Tracey et al. 1987), interleukin (IL)-1 (Dinarello and Thompson 1991), interferon (IFN)-γ (Heinzel 1990), nitric oxide (Dinapoli et al. 1996), and macrophage migration inhibitory factor (MIF) (Calandra et al. 2000; Hotchkiss and Karl 2003; Riedemann et al. 2003 b).

A ubiquitous protein, high mobility group box 1 (HMGB1), is released by activated macrophages/monocytes (Chen et al. 2004; Rendon-Mitchell et al. 2003; Tang et al. 2006; Wang et al. 1999), and functions as a late mediator of lethal endotoxemia and sepsis (Wang et al. 1999; Wang et al. 2004b; Wang et al. 2004c; Yang et al. 2004). Circulating HMGB1 levels are elevated in a delayed fashion (after 16-32 h) in endotoxemic and septic mice (Wang et al. 1999; Yang et al. 2004), and in patients with sepsis (Wang et al. 1999). Administration of recombinant HMGB1 to mice recapitulates many clinical signs of sepsis, including fever (O'Connor et al. 2003), derangement of intestinal barrier function (Sappington et al. 2002), tissue injury (Abraham et al. 2000), and multiple organ failure (Wang et al. 1999). Administration of anti-HMGB1 antibodies or inhibitors (e.g., ethyl pyruvate, nicotine, or stearoyl lysophosphatidylcholine) significantly protects mice against LPS-induced acute tissue injury (Abraham et al. 2000; Ueno et al. 2004), and lethal endotoxemia (Chen et al. 2005; Wang et al. 1999; Wang et al. 2004b; Wang et al. 2004a). Notably, these anti-HMGB1 reagents are capable of rescuing mice from lethal experimental sepsis even when the first doses are given 24 h after the onset of sepsis (Qin et al. 2006; Ulloa et al. 2002; Wang et al. 2004b; Yang et al. 2004), indicating a wider window for HMGB1-targeted therapeutic strategies. Therefore, agents proven clinically safe, and yet still capable of attenuating HMGB1 release may hold potential in the prevention and treatment of inflammatory diseases.

Throughout human history, herbal medicine has formed the basis of folk remedies for various inflammatory ailments. The use of willow bark extract to reduce pain and fever was documented by a Greek physician (Hippocrates) in the 5th century BC, and the subsequent discovery of salicylic acid as its pain/fever-relief active component gave rise to the first synthetic non-steroidal anti-inflammatory drug (NSAID)—aspirin, and the birth of the pharmaceutical industry. Among thousands of Chinese medicinal herbs, only a few have been entitled "Shen" [e.g., Ren Shen (ginsen), Dan Shen (*Salvia miltiorrhiza*)]. Danshen refers to a medicinal herb (termed "shen") containing substance of premier medicinal value (termed "Dan", cinnabar), and has been widely used in China for patients with cardiovascular disorders (Ji et al. 2000). Its beneficial effects are attributable to several red pigments including tanshinone I, II, IV, and cryptotanshinone (Wu et al. 1993; Yagi et al. 1994), which exhibit various anti-inflammatory properties (Jang et al. 2003; Kang et al. 2000; Kim et al. 2002).

Several lines of evidence suggest some anti-inflammatory activities for a number of Danshen components (such as tanshinone I, II, and IV) (Jang et al. 2003; Kang et al. 2000; Kim et al. 2002; Li and Tang 1991; Shilin et al. 1987). Therefore, there is a need for further characterization of the effect of these compounds, or derivatives thereof, on inflammation and the release of mediators of inflammation, particularly the "late" inflammatory mediators. The present invention addresses that need.

SUMMARY OF THE INVENTION

Accordingly, the inventors have discovered that tanshinones are useful in prevention and treatment of inflammation caused by proinflammatory cytokines.

Thus, the invention is directed to methods of attenuating release of a proinflammatory cytokine from a mammalian cell. The methods comprise contacting the cell with a water-soluble tanshinone in an amount effective to attenuate release of the proinflammatory cytokine from the cell.

The invention is also directed to methods of inhibiting an inflammatory cytokine cascade in a mammal. The methods comprise treating the mammal with a water-soluble tanshinone in an amount effective to inhibit the inflammatory cytokine cascade. In these methods, the mammal has a condition mediated by an inflammatory cytokine cascade.

Additionally, the invention is directed to methods of treating an inflammatory cytokine cascade in a mammal. The methods comprise treating the mammal with a tanshinone in an amount effective to inhibit the inflammatory cytokine cascade. In these methods, the mammal has a condition mediated by an inflammatory cytokine cascade.

The invention is further directed to methods of treating a mammal at risk for sepsis, septicemia, shock, and/or endotoxic shock. The methods comprise treating the mammal with tanshinone IIA sodium sulfonate in a manner effective to reduce or prevent a physiologic effect of the endotoxic shock.

The invention is further directed to methods of treating a mammal undergoing sepsis, septicemia, and/or endotoxic shock. The methods comprise administering to the mammal a purified tanshinone in a manner effective to reduce or prevent a physiologic effect of the sepsis, septicemia, and/or endotoxic shock.

The invention is also directed to additional methods of treating a mammal undergoing sepsis, septicemia, and/or endotoxic shock. The methods comprise treating the mammal with a composition comprising *Salvia miltiorrhiza* or an extract thereof in a manner effective to reduce or prevent a physiologic effect of the sepsis. In these methods, the composition does not comprise lignum dalbergiae odoriferae.

The invention is additionally directed to methods of attenuating NO release from a mammalian cell. The methods comprise contacting the cell with a water-soluble tanshinone in an amount effective to attenuate release of NO from the cell.

The invention is further directed to methods of attenuating NO production in a mammal at risk for a disorder mediated by excessive NO production. The methods comprise administering a water-soluble tanshinone to the mammal in an amount effective to attenuate NO production in the mammal.

Additionally, the invention is directed to methods of attenuating NO production in a mammal having a disorder mediated by excessive NO production. The methods comprise administering a purified tanshinone to the mammal in an amount effective to attenuate NO production in the mammal.

BRIEF DESCRIPTION OF THE DRAWINGS

FIG. 2 is graphs and photographs of western blots showing TSNIIA-SS specifically abrogates endotoxin-induced HMGB1 release. Murine macrophage-like RAW 264.7 cells, primary murine peritoneal macrophages, or human peripheral blood mononuclear cells were stimulated with LPS in the absence, or presence of TSNIIA-SS at indicated concentrations. At 16 hours after LPS stimulation, levels of HMGB1 (Panel A, B), nitric oxide (Panel A), or TNF (Panel B, C) in the culture medium were determined by western blotting analysis (Panel A, B), Griess reaction (Panel A), ELISA (Panel B), or cytokine array (Panel C), respectively. Note that at concentrations that completely abrogated LPS-induced HMGB1 release, TSNIIA-SS did not completely block LPS-induced release of nitric oxide (Panel A), TNF (Panel B), IL-1α, PF-4, IL-12 (p70) and MCP-5 (Panel C). Shown in Panel C is a representative cytokine array of two independent experiments with similar results.

FIG. 5 is chemical structures, a photograph of a western blot and a graph showing that TSNIIA-SS attenuates LPS-induced HMGB1 release using a glucocorticoid receptor-independent mechanism. Murine macrophage-like RAW 264.7 cells were stimulated LPS in the absence, or presence, of dexamethasone, cortisone, or TSNIIA-SS alone, or in combination with a glucocorticoid receptor antagonist, RU486. At 16 hours after stimulation, levels of HMGB1 (Panel B) or TNF (Panel C) in the culture medium were determined by western blotting analysis and ELISA, respectively. Panel B is a representative western blot of two independent experiments with similar results. *, P<0.05 versus LPS alone; #, P<0.05 versus "+LPS+Dex".

FIG. 7 is a graph, a photograph of a western blot and micrographs showing that TSNIIA-SS attenuates sepsis-induced systemic HMGB1 accumulation (Panel A) and hepatic injury (Panel B). Balb/C mice were subjected to lethal sepsis by CLP, and intraperitoneally administered with control saline (0.2 ml/mouse) or TSNIIA-SS (at indicated doses) at +24, +48 hours post CLP. At 52 hours post the onset of sepsis, serum HMGB1 levels (Panel A) were determined, and expressed as mean±SD (n=10). *, P<0.05 (ANOVA, Tukey test). In parallel experiments, animals were sacrificed at 48 hours after CLP, and various tissues were sectioned, and stained with hematoxylin and eosin (Panel B). Left micrographs, liver of septic mice ("CLP") with necrotic lesions (marked with empty arrows) as indicated by the loss of cells and the structure of hepatic acinus. Right micrographs, liver of septic mice treated with TSNIIA-SS (15 mg/kg) showing central veins (solid arrow) and surrounding near normal hepatocytes.

FIG. 8 is graphs showing that TSNIIA-SS prevents sepsis-induced cardiovascular dysfunction. Male Sprague-Dawley rats (290-310 g) were subjected to lethal sepsis by CLP, and TSNIIA-SS was administered via the femoral venous catheter using a Harvard Pump (Harvard Apparatus, Holliston, Mass.) at 5 hours after CLP. At 20 hours after CLP or sham operation, total peripheral resistance ("TPR"), stroke volume ("SV"), and cardiac output ("CO") were determined using radioactive microspheres as previously described (Yang et al. 2002b). Data are expressed as mean±S.D. (n=6 per group) and compared by one-way ANOVA and the Tukey test. *, P<0.05 versus sham-operated animals ("−"); #, P<0.05 versus CLP animals treated with vehicle ("+CLP").

DETAILED DESCRIPTION OF THE INVENTION

Accordingly, the inventors have discovered that tanshinones are useful in prevention and treatment of inflammation caused by proinflammatory cytokines. See Example.

Thus, the invention is directed to methods of attenuating release of a proinflammatory cytokine from a mammalian cell. The methods comprise contacting the cell with a water-soluble tanshinone in an amount effective to attenuate release of the proinflammatory cytokine from the cell.

Figure 1:
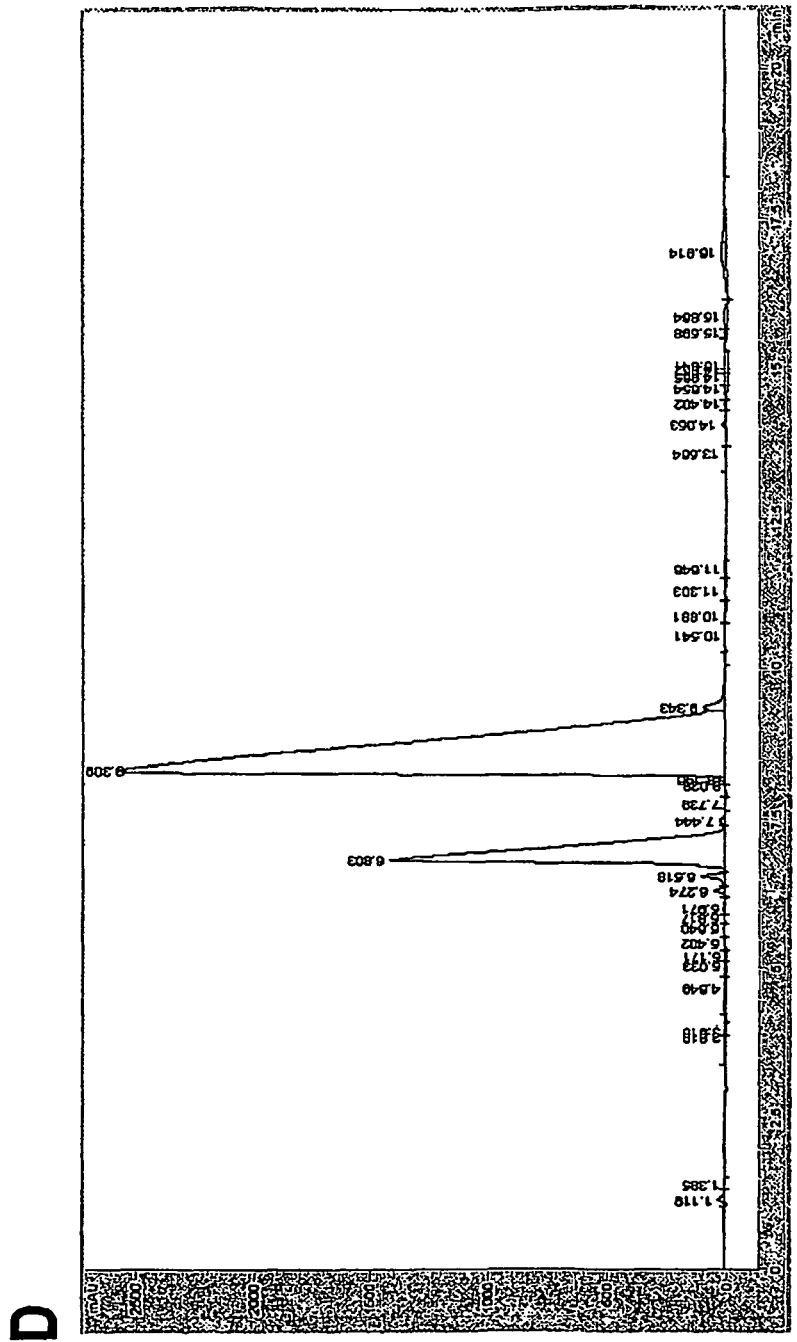
FIG. 1 is graphs, photographs of western blots, and chemical structures showing danshen extract (Panel A) and components (tanshinone I, IIA, and cryptotanshinone, Panel B, C) attenuate endotoxin-induced HMGB1 release. Murine macrophage-like RAW 264.7 cells were stimulated with LPS in the absence, or presence, of herbal extract (Panel A), tanshinone I (TSN I), tanshinone IIA (TSN IIA), or cryptotanshinone (C-TSN) (Panels B, C) for 16 hours, and levels of HMGB1 in the culture medium were determined by western blotting analysis. Below the graphs in Panels A and C is a photograph of a representative western blot of three independent experiments with similar results. *, P<0.05 versus controls (+LPS alone). Panel D shows an HPLC trace of a TSNIIA-SS preparation.

As used herein, a tanshinone is a compound having the hydro-phenanthro[1,2-b]furan-10,11-dione four-ring structure shown in FIG. 1B that can inhibit release of HMGB1 from a macrophage. Examples include the naturally occurring tanshinone I (1,6-Dimethyl-6,7,8,9-tetrahydro-phenanthro[1,2-b]furan-10,11-dione), cryptotanshinone (1,6,6-Trimethyl-1,2,6,7,8,9-hexahydro-phenanthro[1,2-b]furan-10,11-dione), and tanshinone IIA (1,6,6-Trimethyl-6,7,8,9-tetrahydro-phenanthro[1,2-b]furan-10,11-dione) (FIG. 1B). A water-soluble tanshinone has a polar moiety that makes it more soluble than the three naturally occurring tanshinones in FIG. 1B. Non-limiting examples of such polar moieties include sulfonate, amino, nitro, carboxyl, and phosphate groups. The polar moiety can be on the five membered ring as with tanshinone IIA sodium sulfonate (FIG. 1B) or on any other part of the tanshinone, provided the compound continues to have activity inhibiting HMGB1 release. Preferably, the water-soluble tanshinone is a sodium sulfonate derivative of a naturally occurring tanshinone, most preferably tanshinone IIA sodium sulfonate.

These methods are useful with any cell that produces a proinflammatory cytokine. Preferably, the cell is a macrophage.

As shown in Examples 1 and 2 below, tanshinones inhibit release of one or both of the proinflammatory cytokines TNF-α (TNF) and HMGB1, which are preferred proinflammatory cytokines to be affected by the present methods. These methods can also be used to inhibit the release of one or more other proinflammatory cytokines such as interleukin (IL)-1, interferon-γ, and macrophage migration inhibitory factor (MIF).

The cells for these methods may be in a mammal at risk for or having a condition mediated by a proinflammatory cytokine. The method is not limited to any particular mammals, and may be used with mammals residing in zoos or in the wild (e.g., deer, bears, non-human primates etc.), companion mammals (e.g., dogs, cats, hamsters, guinea pigs, ferrets, etc.), farm animals (e.g., cows, pigs, horses, etc.), laboratory animals (rats, mice, etc.), or, preferably, humans.

When treating animals, the tanshinone should be in a pharmaceutically acceptable excipient. By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, excipients, disintegrating agents, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the compound. As used herein, nasally administering or nasal administration includes administering the compound to the mucous membranes of the nasal passage or nasal cavity of the patient. As used herein, pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

Where the compound is administered peripherally such that it must cross the blood-brain barrier, the compound is preferably formulated in a pharmaceutical composition that enhances the ability of the compound to cross the blood-brain barrier of the mammal. Such formulations are known in the art and include lipophilic compounds to promote absorption. Uptake of non-lipophilic compounds can be enhanced by combination with a lipophilic substance. Lipophilic substances that can enhance delivery of the compound across the nasal mucus include but are not limited to fatty acids (e.g., palmitic acid), gangliosides (e.g., GM-1), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™ X-100, and sodium tauro-24,25-dihydrofusidate (STDHF). See Lee et al., Biopharm., April 1988 issue:3037.

In particular embodiments of the invention, the compound is combined with micelles comprised of lipophilic substances. Such micelles can modify the permeability of the nasal membrane to enhance absorption of the compound. Suitable lipophilic micelles include without limitation gangliosides (e.g., GM-1 ganglioside), and phospholipids (e.g., phosphatidylserine). Bile salts and their derivatives and detergent-like substances can also be included in the micelle formulation. The compound can be combined with one or several types of micelles, and can further be contained within the micelles or associated with their surface.

Alternatively, the compound can be combined with liposomes (lipid vesicles) to enhance absorption. The compound can be contained or dissolved within the liposome and/or associated with its surface. Suitable liposomes include phospholipids (e.g., phosphatidylserine) and/or gangliosides (e.g., GM-1). For methods to make phospholipid vesicles, see for example, U.S. Pat. No. 4,921,706 to Roberts et al., and U.S. Pat. No. 4,895,452 to Yiournas et al. Bile salts and their derivatives and detergent-like substances can also be included in the liposome formulation.

Examples of conditions that are mediated by proinflammatory cytokines and that may be usefully treated using the invention methods are appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis; hepatitis, Crohn's disease, ileus, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosus, Goodpasture's syndrome, Behcets's syndrome, allograft rejection, graft-versus-host disease, Type I diabetes, ankylosing spondylitis, Berger's disease, Retier's syndrome, or Hodgkins disease. Preferably, the condition is appendicitis, peptic, gastric or duodenal ulcers, peritonitis, pancreatitis, ulcerative, pseudomembranous, acute or ischemic colitis, hepatitis, rheumatoid arthritis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection and graft-versus-host disease. In the most preferred embodiments, the condition is sepsis, septicemia, and/or endotoxic shock.

The present methods can also further comprise administering a second anti-inflammatory agent to the mammal. Non-limiting examples include an NSAID, a cytokine inhibitor, a salicylate, a COX inhibitor, a COX-2 inhibitor, or a steroid. In particularly preferred methods, the condition is sepsis, septicemia, and/or endotoxic shock and the second treatment is administration of a muscarinic agonist, an adrenomedullin, an adrenomedullin binding protein, a milk fat globule epidermal growth factor VIII, an activated protein C, or an $\alpha_{2A}$-adrenergic antagonist.

The invention is also directed to methods of inhibiting an inflammatory cytokine cascade in a mammal. The methods comprise treating the mammal with a water-soluble tanshinone in an amount effective to inhibit the inflammatory cytokine cascade. In these methods, the mammal has a condition mediated by an inflammatory cytokine cascade.

As with the methods discussed above, the water-soluble tanshinone is preferably a sodium sulfonate derivative of a naturally occurring tanshinone, most preferably tanshinone IIA sodium sulfonate. Any mammal can be the subject of these methods. Preferably, the mammal is a human.

Most preferably, the condition is sepsis, septicemia, and/or endotoxic shock, the mammal is a human and the tanshinone is tanshinone IIA sodium sulfonate.

Additionally, the invention is directed to methods of treating an inflammatory cytokine cascade in a mammal. The methods comprise treating the mammal with a tanshinone in an amount effective to inhibit the inflammatory cytokine cascade. In these methods, the mammal has a condition mediated by an inflammatory cytokine cascade.

Preferably, the tanshinone is a water-soluble tanshinone, more preferably a sodium sulfonate derivative of a naturally occurring tanshinone, most preferably tanshinone IIA sodium sulfonate. Any mammal can be the subject of these methods. Most preferably, the condition is sepsis, septicemia, and/or endotoxic shock, the mammal is a human and the tanshinone is tanshinone IIA sodium sulfonate.

The invention is further directed to methods of treating a mammal at risk for sepsis, septicemia, and/or endotoxic shock. The methods comprise treating the mammal with tanshinone IIA sodium sulfonate in a manner effective to reduce or prevent a physiologic effect of the endotoxic shock. Any physiologic effect of the endotoxic shock can be measured to determine the efficacy of the treatment. Preferred physiologic effects here are HMGB1 release, TNF release, nitric oxide (NO) release, or lethal sepsis. Most preferably, the mammal is a human.

The invention is further directed to methods of treating a mammal undergoing sepsis, septicemia, and/or endotoxic shock. The methods comprise administering to the mammal a purified tanshinone in a manner effective to reduce or prevent a physiologic effect of the sepsis, septicemia, and/or endotoxic shock. Useful tanshinones for these methods include tanshinone I, tanshinone IIA, or cryptotanshinone. More preferred tanshinones are water-soluble tanshinones, most preferably tanshinone IIA sodium sulfonate.

Any physiologic effect of the endotoxic shock can be measured to determine the efficacy of the treatment. Preferred physiologic effects here are HMGB1 release, TNF release, nitric oxide (NO) release, or lethal sepsis. Most preferably, the mammal is a human.

The invention is also directed to additional methods of treating a mammal undergoing sepsis, septicemia, and/or endotoxic shock. The methods comprise treating the mammal with a composition comprising *Salvia miltiorrhiza* or an extract thereof in a manner effective to reduce or prevent a physiologic effect of the sepsis. In these methods, the composition does not comprise lignum dalbergiae odoriferae. The composition may comprise *Salvia miltiorrhiza*, or, preferably, an extract of *Salvia miltiorrhiza* (see Example). Preferred extracts comprise an organic component, where at least 5% by weight of the organic component is a tanshinone. More preferably, at least 10%, even more preferably at least 25%, still more preferably at least 50% or at least 80% by weight of the organic component is a tanshinone. Most preferably, at least 95% by weight of the organic component is a tanshinone.

Any physiologic effect of the endotoxic shock can be measured to determine the efficacy of the treatment. Preferred physiologic effects here are HMGB1 release, TNF release, nitric oxide (NO) release, or lethal sepsis. Most preferably, the mammal is a human.

The invention is additionally directed to methods of attenuating NO release from a mammalian cell. The methods comprise contacting the cell with a water-soluble tanshinone in an amount effective to attenuate release of NO from the cell.

As in the methods described above, a preferred water-soluble tanshinone is a sodium sulfonate derivative of a naturally-occurring tanshinone, most preferably tanshinone IIA sodium sulfonate. Preferably, at least 80% of the tanshinone preparation is sulfonated.

The cell is preferably part of a live mammal at risk for or having a disorder mediated by excessive NO production. Nonlimiting examples of such disorders are shock, ileitis, ulcerative colitis, Crohn's disease, asthma, bronchitis, oxidant-induced lung injury, chronic obstructive airway disease, corneal dystrophy, ocular hypertension, trachoma, onchocerciasis, retinitis, uveitis, sympathetic ophthalmitis, endophthalmitis, periodontitis, arthritis, septic arthritis, osteoarthritis, rheumatoid arthritis, tuberculosis, leprosy, glomerulonephritis sarcoid, nephrosis, sclerodermatitis, sunburn, psoriasis, eczema, amyotrophic lateral sclerosis, sclerosis, dementia including AIDS-related neurodegeneration, Alzheimer's disease, encephalomyelitis, viral or autoimmune encephalitis, immune-complex vasculitis, systemic lupus, erythematosus, ischemic heart disease, heart failure, cardiomyopathy, adrenal insufficiency, hypercholesterolemia, atherosclerosis, osteoporosis, pre-eclampsia, eclampsia, uremic complications, chronic liver failure, stroke, cerebral ischemia, cystic fibrosis, tuberculosis, cachexia, ischemia/reperfusion, hemodialysis related conditions, glomerulonephritis, restenosis, inflammatory sequelae of viral infections, hypoxia, hyperbaric oxygen convulsions and toxicity, dementia, Sydenham's chorea, Parkinson's disease, Huntington's disease, amyotrophic lateral sclerosis (ALS), multiple sclerosis, epilepsy, Korsakoff s disease, imbecility related to cerebral vessel disorder, NO mediated cerebral trauma and related sequelae, ischemic brain edema (stroke), pain, migraine, emesis, immune complex disease, as immunosuppressive agents, acute allograft rejection, or cancer. The most preferred disorders here are sepsis, septicemia, and/or endotoxic shock. Most preferably the mammal is a human.

The invention is further directed to methods of attenuating NO production in a mammal at risk for a disorder mediated by excessive NO production. The methods comprise administering a water-soluble tanshinone to the mammal in an amount effective to attenuate NO production in the mammal. Preferably the water-soluble tanshinone is a sodium sulfonate derivative of a naturally occurring tanshinone, most preferably tanshinone IIA sodium sulfonate.

For these methods, preferred disorders are a shock, ileitis, ulcerative colitis, Crohn's disease, asthma, bronchitis, oxidant-induced lung injury, chronic obstructive airway disease, corneal dystrophy, ocular hypertension, trachoma, onchocerciasis, retinitis, uveitis, sympathetic ophthalmitis, endophthalmitis, periodontitis, arthritis, septic arthritis, osteoarthritis, rheumatoid arthritis, tuberculosis, leprosy, glomerulonephritis sarcoid, nephrosis, sclerodermatitis, sunburn, psoriasis, eczema, amyotrophic lateral sclerosis, sclerosis, dementia including AIDS-related neurodegeneration, Alzheimer's disease, encephalomyelitis, viral or autoimmune encephalitis, immune-complex vasculitis, systemic lupus, erythematosus, ischemic heart disease, heart failure, cardiomyopathy, adrenal insufficiency, hypercholesterolemia, atherosclerosis, osteoporosis, pre-eclampsia, eclampsia, uremic complications, chronic liver failure, stroke, cerebral ischemia, cystic fibrosis, tuberculosis, cachexia, ischemia/reperfusion, hemodialysis related conditions, glomerulonephritis, restenosis, inflammatory sequelae of viral infections, hypoxia, hyperbaric oxygen convulsions and toxicity, dementia, Sydenham's chorea, Parkinson's disease, Huntington's disease, amyotrophic lateral sclerosis (ALS), multiple sclerosis, epilepsy, Korsakoff s disease, imbecility related to cerebral vessel disorder, NO mediated cerebral trauma and related sequelae, ischemic brain edema (stroke), pain, migraine, emesis, immune complex disease, as immunosuppressive agents, acute allograft rejection, or cancer. Most preferably, the disorder is sepsis, septicemia, and/or endotoxic shock. The mammal is preferably a human.

Additionally, the invention is directed to methods of attenuating NO production in a mammal having a disorder mediated by excessive NO production. The methods comprise administering a purified tanshinone to the mammal in an amount effective to attenuate NO production in the mammal. Preferably, the tanshinone is tanshinone I, tanshinone IIA, or cryptotanshinone, more preferably a water-soluble tanshinone, most preferably tanshinone IIA sodium sulfonate.

For these methods, preferred disorders are a shock, ileitis, ulcerative colitis, Crohn's disease, asthma, bronchitis, oxidant-induced lung injury, chronic obstructive airway disease, corneal dystrophy, ocular hypertension, trachoma, onchocerciasis, retinitis, uveitis, sympathetic ophthalmitis, endophthalmitis, periodontitis, arthritis, septic arthritis, osteoarthritis, rheumatoid arthritis, tuberculosis, leprosy, glomerulonephritis sarcoid, nephrosis, sclerodermatitis, sunburn, psoriasis, eczema, amyotrophic lateral sclerosis, sclerosis, dementia including AIDS-related neurodegeneration, Alzheimer's disease, encephalomyelitis, viral or autoimmune encephalitis, immune-complex vasculitis, systemic lupus, erythematosus, ischemic heart disease, heart failure, cardiomyopathy, adrenal insufficiency, hypercholesterolemia, atherosclerosis, osteoporosis, pre-eclampsia, eclampsia, uremic complications, chronic liver failure, stroke, cerebral ischemia, cystic fibrosis, tuberculosis, cachexia, ischemia/reperfusion, hemodialysis related conditions, glomerulonephritis, restenosis, inflammatory sequelae of viral infections, hypoxia, hyperbaric oxygen convulsions and toxicity, dementia, Sydenham's chorea, Parkinson's disease, Huntington's disease, amyotrophic lateral sclerosis (ALS), multiple sclerosis, epilepsy, Korsakoff s disease, imbecility related to cerebral vessel disorder, NO mediated cerebral trauma and related sequelae, ischemic brain edema (stroke), pain, migraine, emesis, immune complex disease, as immunosuppressive agents, acute allograft rejection, or cancer. Most preferably, the disorder is sepsis, septicemia, and/or endotoxic shock. The mammal is preferably a human.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE

A Cardiovascular Drug Rescues Mice from Lethal Sepsis by Selectively Attenuating a Late-Acting Proinflammatory Mediator, HMGB1

Example Summary

The pathogenesis of sepsis is mediated in part by bacterial endotoxin, which stimulates macrophages/monocytes to sequentially release early (e.g., TNF, IL-1, and IFN-□) and late (e.g., HMGB1) pro-inflammatory cytokines. The recent discovery of HMGB1 as a late mediator of lethal sepsis has prompted investigation for development of new experimental therapeutics. We found that many steroidal (such as dexamethasone and cortisone) and non-steroidal anti-inflammatory drugs (such as aspirin, ibuprofen, and indomethacin) failed to influence endotoxin-induced HMGB1 release even at superpharmacological concentrations (up to 10-25 □M). However, several steroid-like pigments (tanshinone I, tanshinone IIA, and cryptotanshinone) of a popular Chinese herb, Danshen (Saliva miltiorrhizae), dose-dependently attenuated endotoxin-induced HMGB1 release in macrophage/monocyte cultures. A water-soluble tanshinone IIA derivative (sodium sulfonate), TSNIIA-SS, which has been widely used as a Chinese medicine for patients with cardiovascular disorders, selectively abrogated endotoxin-induced-HMGB1 cytoplasmic translocation and release in a glucocorticoid receptor-independent manner. Administration of TSNIIA-SS significantly protected mice against lethal endotoxemia, and rescued mice from lethal sepsis even when the first dose was given 24 hours after the onset of sepsis. The therapeutic effects were partly attributable to: 1) attenuation of systemic accumulation of HMGB1 (but not TNF and nitric oxide); 2) prevention of hepatic injury; and 3) improvement of cardiovascular physiologic parameters (e.g., decrease in total peripheral vascular resistance, and increase in cardiac stroke volume) in septic animals. Taken together, these data re-enforce the pathogenic role of HMGB1 in lethal sepsis, and support a therapeutic potential for TSNIIA-SS in the treatment of human sepsis.

Introduction

As demonstrated below, Danshen extract, as well as several components (tanshinone I, tanshinone IIA, and cryptotanshinone), significantly attenuate HMGB1 release from bacterial endotoxin-stimulated macrophage cultures. Treatment of animals with a water-soluble tanshinone IIA derivative (tanshinone IIA sodium sulfonate) significantly attenuated systemic accumulation of HMGB1 in endotoxemia and sepsis, and conferred a dose-dependent protection against lethal endotoxemia, and sepsis, even when the first dose of tanshinone IIA sodium sulfonate is administered 24 hours after the onset of sepsis.

Materials and Methods

Cell culture. Murine macrophage-like RAW 264.7 cells were obtained from the American Type Culture Collection (ATCC, Rockville, Md.), and primary peritoneal macrophages were isolated from Balb/C mice (male, 7-8 weeks, 20-25 grams) at 2-3 days after intraperitoneal injection of 2 ml thioglycollate broth (4%) as previously described (Chen et al. 2004; Rendon-Mitchell et al. 2003). Murine macrophages were pre-cultured in RPMI 1640 medium (Gibco BRL, Grand Island, N.Y.) supplemented with 10% fetal bovine serum (FBS) and 2 mmol/L glutamine. Human peripheral blood mononuclear cells (HuPBMCs) were isolated from the blood of healthy donors (Long Island Blood Bank, Melville, N.Y.) by density gradient centrifugation through Ficoll (Ficoll-Paque PLUS, Pharmacia, Piscataway, N.J.), and cultured in RPMI 1640 supplemented with 10% heat-inactivated human serum/0.2 mM L-glutamine as previously described (Rendon-Mitchell et al. 2003).

LPS stimulation. Adherent macrophages or monocytes were gently washed with, and cultured in, serum-free OPTI-MEM I medium two hours before stimulation with bacterial endotoxin (lipopolysaccharide, LPS, $E.\ coli$ 0111:B4, Sigma-Aldrich). At 16 hours after LPS stimulation, levels of HMGB1 in the culture medium were determined as previously described (Chen et al. 2004; Rendon-Mitchell et al. 2003; Wang et al. 1999).

Preparation of Herbal Extract. Various Chinese Herbs were Obtained from NY-Tongrentang, Inc. (Flushing, N.Y., USA), and extracted in water (85° C.) for 4 h. The water-soluble fraction was cleared sequentially by centrifugation (3300 g, 20 min, 4° C.) and filtration (through a 0.2 μm filter), and the filtrate fraction was examined for HMGB1-suppressing activities.

Chemical-sources and stock solutions. Dexamethasone, cortisone, and RU486 were obtained from the Sigma (St. Louis, Mo.), and 10 mM stock solutions were prepared in 100% ethanol. Aspirin (Cat. No. A0819), ibuprofen (Cat. No. I0481), indomethacin (Cat. No. I5315) were obtained from the LKT Laboratories Inc. (St Paul, Minn., USA), and 10 mM stock solution were prepared in water (20 mM). Tanshinone I (Cat. No. T0153, 98.6% HPLC purity), tanshinone IIA (Cat. No. T0154, 93.0% HPLC purity), and cryptotanshinone (Cat. No. C7097, 98.8% HPLC purity) were obtained from the LKT Laboratories Inc., and 20 mM stock solutions were prepared in dimethylsulfoxide (DMSO). Tanshinone IIA sodium sulfonate (TSNIIA-SS) was obtained from the Shanghai No. 1 Biochemical & Pharmaceutical Co., LTD (Shanghai, P. R. China), and its purity was determined by HPLC using a Nova-pak C18 column (3.9×150 mm) and 0.065% trifluoroacetic acid (TFA, v/v, in water) as the mobile phase. The sample was eluted by a linear gradient of 0-59% acetonitrile (v/v, in 0.065% TFA) over 12 minutes at a flow rate of 1.0 ml/min, and monitored at a wavelength of 452.2 nm. Each HPLC peak was analyzed using a Liquid Chromatography-Mass Spectrometry (LC-MS, LCQ DECA XPPLUS, Thermo Electron Corporation). The major peak (at a retention time of 8.3 min) accounted for >80% of the total area under the HPLC peaks (FIG. 1D), and contained a red pigment with an m/z=373.07 (100.0%), corresponding to an empirical formula of $C_{19}H_{17}O_6S$-(tanshinone IIA sulfonate).

Animal models of endotoxemia and sepsis. This study was approved and performed in accordance with the guidelines for the care and use of laboratory animals at the Feinstein Institute for Medical Research, Manhasset, N.Y. Endotoxemia was induced in Balb/C mice (male, 7-8 weeks) by intraperitoneal injection of bacterial endotoxin (LPS, 15 mg/kg) as previously described (Chen et al. 2005; Wang et al. 1999; Wang et al. 2006). Sepsis was induced in male Balb/C mice (7-8 weeks, 20-25 g) or Sprague-Dawley rats (290-310 g) by cecal ligation and puncture (CLP) as previously described (Wang et al. 2006; Yang et al. 2002b). Herbal components were administered intraperitoneally into mice at indicated doses and time points, and mice were monitored for survival for up to two weeks. In parallel experiments, mice were euthanized to collect blood at 28 h (following two doses of herbal components at −0.5 and +24 h) after endotoxemia, and at 52 h (following two doses of herbal components at +24 and +48 h) after CLP.

TNF ELISA. The levels of TNF in the culture medium or serum were determined using commercial enzyme linked immunosorbent assay (ELISA) kits (Catalog no. MTA00, R & D Systems, Minneapolis, Minn.) with reference to standard curves of purified recombinant TNF at various dilutions as previously described (Chen et al. 2004; Rendon-Mitchell et al. 2003; Wang et al. 2006).

Nitric oxide assay. The levels of nitric oxide in the culture medium were determined indirectly by measuring $NO^{2-}$ production with a colorimetric assay based on the Griess reaction (Rendon-Mitchell et al. 2003). NO2-concentrations were determined with reference to a standard curve generated with sodium nitrite at various dilutions.

HMGB1 western blotting analysis. The levels of HMGB1 in the culture medium or serum were determined by western blotting analysis as previously described (Chen et al. 2004; Rendon-Mitchell et al. 2003; Wang et al. 1999). The relative band intensity was quantified using NIH image 1.59 software to determine HMGB1 levels with reference to standard curves generated with purified HMGB1.

Cytokine antibody array. Murine cytokine antibody array (Cat. No. M0308003, RayBiotech Inc., Norcross, Ga., USA), which detects 62 cytokines on one membrane, was used to determine the profile of cytokines in the culture medium following the manufacturer's instructions. Briefly, the membranes were sequentially incubated with equal volume of cell-conditioned culture medium, primary biotin-conjugated antibody, and horseradish peroxidase-conjugated streptavidin. After exposing to X-ray film, the relative signal intensity was determined using the NIH image 1.59 software with reference to the positive controls on the membrane.

Immunocytochemistry and cell fractionation/western blot. At 16 h after LPS stimulation, cellular HMGB1 was immunostained with anti-HMGB1 polyclonal antibodies, and images were acquired using fluorescent microscope (Carl Zeiss Microimaging, Inc., Thornwood, N.Y.) as previously described (Chen et al. 2004; Rendon-Mitchell et al. 2003). Alternatively, localization of HMGB1 was examined by a cell fractionation/western blotting technique as previously described (Tang et al. 2006). Cell fractionation is based on differential lysis of plasma and nuclear membranes by non-ionic detergent (NP-40). Briefly, after selective lysis of the plasma membrane in low salt buffer (10 mM HEPES, pH 7.9; 10 mM KCl; 0.1 mM EDTA; 0.1 mM EGTA; 1 mM DTT; 0.5 mM PMSF, 1% NP-40), the intact nuclei was collected by a quick centrifugation step (7,000 g, 1 min, 4° C.), leaving the cytoplasmic fraction in the supernatant. The nuclei pellet was resuspended in NP-40 high salt buffer (20 mM HEPES, pH 7.9; 0.4 M NaCl; 1 mM EDTA; 1 mM EGTA; 1 mM DTT; 1 mM PMSF, 1% NP-40), and briefly sonicated to generate the nuclear fraction. After fractionation, the protein content of different fractions was determined by the Bradford method, and each fraction was assayed for levels of various protein by western blotting analysis using primary antibodies specific for HMGB1, a cytoplasmic protein (βactin, Santa Cruz Biotechnology), and a nuclear protein (PCNA, BD Biosciences).

Cell Viability Assays. Cell viability was assessed by trypan blue exclusion assays as previously described (Rendon-Mitchell et al. 2003). Briefly, trypan blue was added to cell cultures at a final concentration of 0.08%. After incubation for 5 min at 25° C., cell viability was assessed by the percentage of dye-excluding cells in five 40× microscope fields.

Tissue histology. At 48 hours after CLP, mice were euthanized in CO2 Chamber, and immediately perfused (transcardially) with phosphate buffer saline and 4% paraformaldehyde. Various tissues were harvested, sectioned, and stained with hematoxylin and eosin for morphology evaluation.

Measurement of cardiac output. A radiolabeled microsphere technique was used to measure cardiac output at 20 h after CLP or sham operation as previously described (Yang et al. 2002b). Briefly, a bolus of $^{141}Ce$-labeled microspheres (4.0 µCi, DuPont NEN, Boston, Mass.) was injected into the left ventricle, where it mixed uniformly with the oxygenated blood at the root of the aorta, and subsequently distributed via aortic blood flow to the capillary beds within each organ. The reference blood sample was withdrawn from the femoral arterial catheter (at a rate of 0.7 ml/min) with a pump (Harvard Apparatus, Holliston, Mass.), after which isotonic sodium chloride solution was infused manually to replace the volume of blood lost. At 20 h post CLP, animals were sacrificed to harvest various organs for measurement of radioactivity with an automatic gamma counter (1470 Wizard; Wallac, Gaithersburg, Md.). Cardiac output and organ blood flow were calculated according to the following equations: cardiac output=[(RBF×CT)/Cr]×1/100 and organ blood flow=[(RBF× Ct)/Cr]×1/100, where RBF is the reference blood sample withdrawal rate (0.7 ml/min), CT is counts per minute of total injected dose, Ct is counts per minute per gram of tissue, and Cr is counts per minute in the reference blood sample. Stroke volume (SV) and total peripheral resistance (TPR) were calculated as previously described (Yang et al. 2002b).

Statistical Analysis. Data are expressed as mean±SD of two independent experiments in triplicates (n=2). One-way ANOVA was used for comparison among all different groups. When the ANOVA was significant, post-hoc testing of differences between groups was performed using Tukey's test. The Kaplan-Meier method was used to compare the differences in mortality rates between groups. A P value less than 0.05 was considered statistically significant.

Results

Danshen (Saliva miltiorrhizae) extract and components attenuate endotoxin-induced HMGB1 release. The successful identification of salicylic acid as the active principle of willow bark to reduce fever and pain gave rise to the first synthetic non-steroidal anti-inflammatory drug (NSAID)—aspirin. Many NSAIDs (such as aspirin, ibuprofen, and indomethacin) can inhibit cyclooxygenases, but are unable to protect animals against lethal sepsis (Hasselgren et al. 1985; Noronha-Blob et al. 1993; Villa et al. 1995). None of the tested cyclooxygenase inhibitors (e.g., aspirin, ibuprofen, and indomethacin) significantly affected LPS-induced HMGB1 release even at superpharmacological concentrations (1-25 μM, data not shown). Twenty-five medicinal herbs were also tested. Danshen (Saliva miltiorrhizae) extract dose-dependently attenuated endotoxin-induced HMGB1 release (FIG. 1A).

To determine Danshen's active principle(s), its anti-inflammatory components were examined for HMGB1-inhibiting activities. One potential anti-inflammatory component, ferulic acid, effectively attenuated LPS-induced nitric oxide production, but failed to affect LPS-induced HMGB1 release (Wang et al. 2006). Danshen also contains abundant red pigments (termed tanshinone I, tanshinone IIA, and cryptotanshinone) (FIG. 1B), a group of substance with medicinal value for patients with cardiovascular abnormalities (Ji et al. 2000). All three tanshinones (I, IIA, and cryptotanshinone) effectively attenuated LPS-induced HMGB1 release, with an estimated IC50<25 μM (FIG. 1C).

Water-soluble tanshinone IIA sodium sulfonate (TSNIIA-SS) selectively attenuates endotoxin-induced HMGB1 release. Most tanshinones are barely water-soluble at physiological temperature, and this poor solubility may adversely affect their bioavailability in vivo. We thus examined a water-soluble tanshinone IIA derivative, TSNIIA-SS (FIG. 1B), for HMGB1-inhibiting activities. TSNIIA-SS is a widely used Chinese medicine for patients with cardiovascular disorders (Ji et al. 2000), and was obtained from the Shanghai No. 1 Biochemical & Pharmaceutical Co., LTD. HPLC analysis (FIG. 1D) revealed a major peak (>80%, at a retention time of 8.3 min) containing a red pigment with an m/z=373.07, corresponding to an empirical formula of C19H17O6S-(tanshinone IIA sulfonate). The minor HPLC peak (<20%, at a retention time of 6.8 min) contained a red pigment with an m/z=389.11, corresponding to an empirical formula of C19H17O7S-(an unknown analogue of tanshinone IIA sulfonate). The highly purified TSNIIA-SS (>99.0% by HPLC) dose-dependently inhibited HMGB1 release, with an estimated $IC_{50}$ of <5 μM (FIG. 2A). Similarly, it effectively inhibited LPS-induced HMGB1 release in cultures of primary human peripheral blood mononuclear cells (FIG. 2B), and murine peritoneal macrophages (data not shown).

To further evaluate its anti-inflammatory properties, its potential effects were determined on LPS-induced release of other proinflammatory mediators. At concentrations (100 μM) that completely abrogated LPS-induced HMGB1 release, TSNIIA-SS did not completely block LPS-induced release of nitric oxide (FIG. 2A, lower panel) or TNF (FIG. 2B, lower panel). Furthermore, its inhibitory effects on TNF (but not HMGB1) release were often lost when macrophages were stimulated with LPS at higher concentrations (>200 ng/ml), indicating selectivity for HMGB1 suppression. To evaluate this specificity, its effects on the release of 62 cytokines were determined using a cytokine protein array. At concentrations that completely abrogated LPS-induced HMGB1 release (100 μM, data not shown), TSNIIA-SS did not suppress the release of most cytokines, including IL-6, IL-12p40/ p70, KC, MCP-1, MIP-1α, MIP-1γ, MIP-2 and TNF, in RAW 264.7 cells (FIG. 2C, upper row), or primary peritoneal macrophages (FIG. 2C, lower row). Consistent with a previous report (Kang et al. 2000), TSNIIA-SS only partially attenuated LPS-induced release of IL-12p70 (by 45±5%), along with a few other cytokines, such as IL-1α (by 50±7%), platelet factor 4 (PF-4, by 35±6%), and MCP-5 (by 25±5%). Taken together, these data indicate that TSNIIA-SS selectively attenuates LPS-induced release of HMGB1 as opposed to other proinflammatory cytokines.

Figure 3:
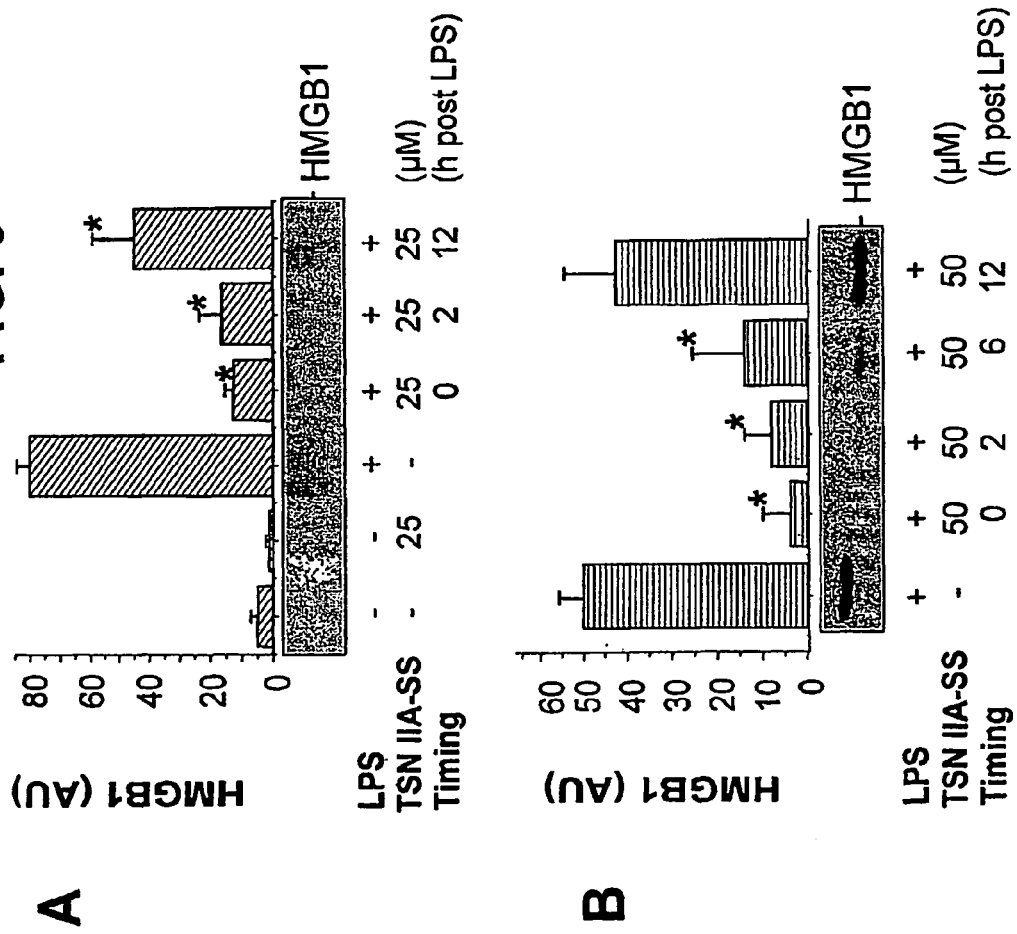
FIG. 3 is graphs and photographs of western blots showing that delayed administration of TSNIIA-SS still significantly attenuates endotoxin-induced HMGB1 release. Murine macrophage-like RAW 264.7 cells were stimulated with LPS, and TSNIIA-SS (25 µM, or 50 µM) was added at 0, 2, 6, and 12 hours post LPS stimulation. Levels of HMGB1 levels in the culture medium were determined at 16 hours after LPS stimulation, and expressed (in arbitrary unit, AU) as mean±S.D. of two independent experiments (N=2). Below each graph is a representative western blot. *, P<0.05 versus controls (+LPS alone).

Delayed administration of TSNIIA-SS significantly attenuates endotoxin-induced HMGB1 release. As compared with early proinflammatory cytokines (such as TNF), HMGB1 is released in a delayed fashion following endotoxin stimulation. It is intriguing to consider whether TSNIIA-SS can inhibit HMGB1 release if added after LPS stimulation. Whereas concurrent administration of TSNIIA-SS with LPS was maximally effective in suppressing HMGB1 release, significant inhibition was retained when it was added 2 to 6 h after LPS (FIG. 3). It may thus be feasible to pharmacologically attenuate late-acting proinflammatory mediators (such as HMGB1) by strategically administering TSNIIIA-SS in a delayed fashion.

Figure 4:
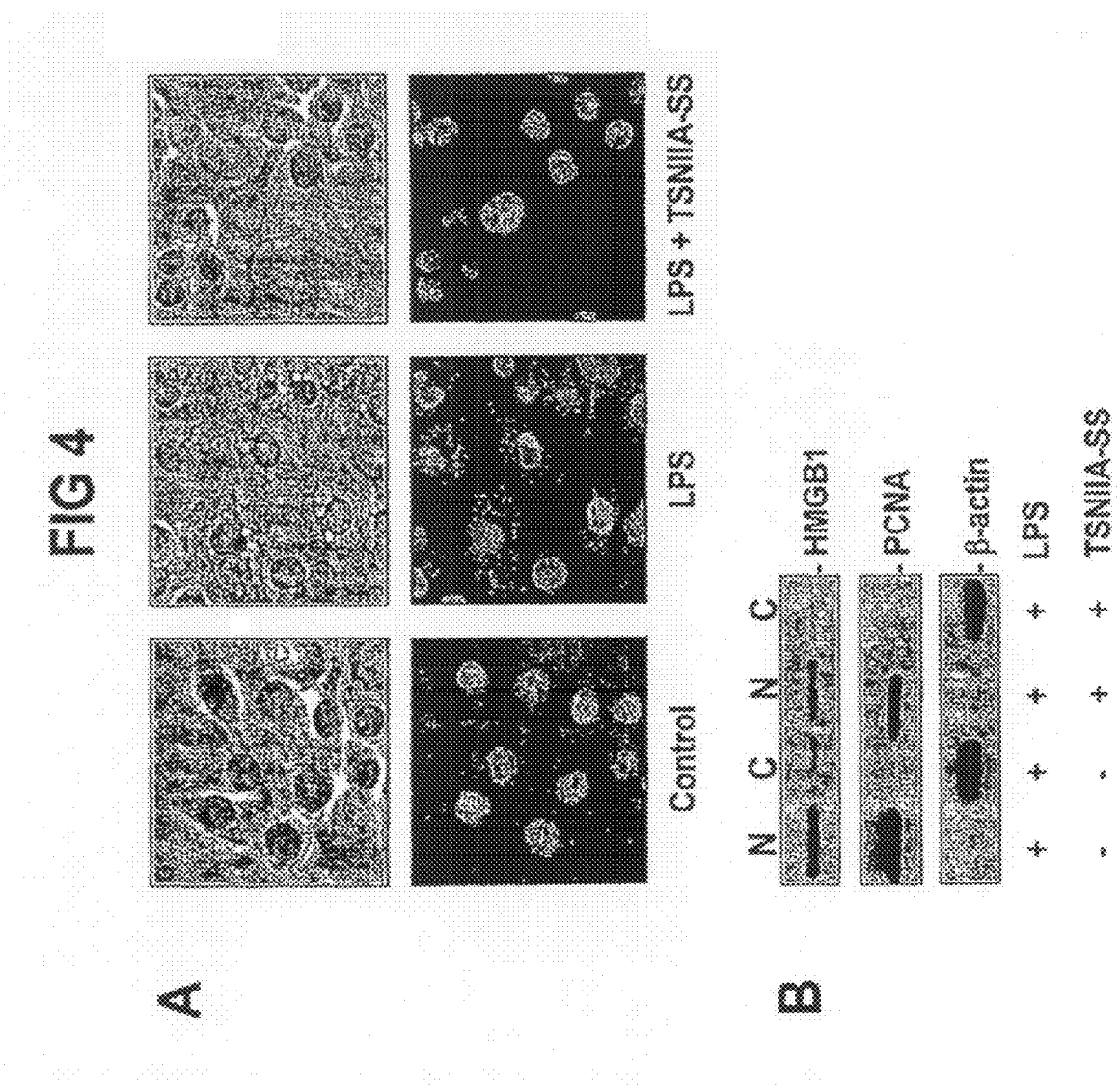
FIG. 4 is micrographs and photographs of western blots showing that TSNIIA-SS blocks endotoxin-induced cytoplasmic HMGB1 translocation. Macrophage cultures were stimulated with LPS in the absence, or presence, of TSNIIA-SS, and assayed for HMGB1 cytoplasmic translocation by immunohistochemistry (Panel A), or cell fractionation/Western blot (Panel B) at 16 h post LPS stimulation. Note that HMGB1 was predominantly localized in the nuclear region of un-stimulated macrophages ("control", Panel A, left panels), in both cytoplasmic and nuclear regions of LPS-stimulated macrophages (Panel A, middle photographs). TSNIIA-SS (100 µM) preserved HMGB1 in the nuclear regions (Panel A, right photographs). Following LPS stimulation, cytoplasmic ("C") and nuclear ("N") fractions were isolated, and assayed for levels of HMGB1, a nuclear (PCNA), or cytoplasmic (β-actin) protein by western blotting analysis. Equal loading of samples was confirmed by western blotting analysis of fractions with cytoplasmic (β-actin) or nuclear (PCNA) protein markers. Blots are representative of two independent experiments with similar results.

TSNIIA-SS inhibits endotoxin-induced HMGB1 release by blocking its cytoplasmic translocation. To investigate the mechanism of tanshinone-mediated suppression of HMGB1 release, its effect was determined on endotoxin-induced HMGB1 cytoplasmic translocation—an essential step for HMGB1 release (Chen et al. 2004; Gardella et al. 2002; Rendon-Mitchell et al. 2003). Consistent with previous reports (Chen et al. 2004), quiescent macrophages constitutively expressed HMGB1 and maintained an intracellular "pool" of HMGB1 predominantly in the nucleus (FIG. 4A, left micrographs). At 16 h post LPS stimulation, significant HMGB1 staining in cytoplasmic vesicles was observed (FIG. 4A, middle micrographs), confirming that LPS stimulates macrophages to actively translocate nuclear HMGB1 to the cytoplasm before releasing it into the extracellular milieu. Although the TSNIIA-SS did not affect the nuclear localization of HMGB1 in resting cells (data not shown), it almost completely abrogated LPS-induced HMGB1 cytoplasmic translocation in most endotoxin-stimulated cells (FIG. 4A, right micrographs), indicating that TSNIIA-SS attenuates HMGB1 release by interfering with its cytoplasmic translocation.

To further validate the above hypothesis, cytoplasmic and nuclear fractions were isolated, and immunoblotted with antibodies specific for HMGB1, PCNA (a nuclear protein), or β-actin (a cytoplasmic protein), respectively. Consistently, levels of HMGB1 in the cytoplasmic fractions were dramatically increased after LPS stimulation (data not shown), but were dramatically reduced by TSNIIA-SS treatment (FIG. 4B), confirming that TSNIIA-SS attenuates HMGB1 release by interfering with its cytoplasmic translocation.

TSNIIA-SS inhibits endotoxin-induced HMGB1 release in a glucocorticoid receptor-independent mechanism. In light of the structural resemblance (i.e., the presence of a four-fused-ring structure) between tanshinones and steroidal anti-inflammatory drugs (FIG. 5A), it was evaluated: 1) whether corticosteroids similarly attenuated LPS-induced HMGB1 release; and 2) whether TSNIIA-SS abrogates HMGB1 release in a glucocorticoid receptor-dependent mechanism. Even at concentrations up to 10 μM, dexamethasone and cortisone failed to reduce LPS-induced HMGB1 release (FIG. 5B), although they effectively attenuated LPS-mediated TNF secretion (FIG. 5C). Steroidal anti-inflammatory drugs inhibit cytokines through binding to intracellular glucocorticoid receptor (Waage et al. 1990), which can be overridden by specific glucocorticoid receptor antagonists (such as RU486). Indeed, RU486 almost completely abrogated dexamethasone-mediated suppression of TNF secretion (FIG. 5C), but did not affect TSNIIA-SS-mediated inhibition of TNF (FIG. 5C), or HMGB1 release (data not shown). Taken together, these data indicate that TSNIIA-SS and dexamethasone utilize distinct mechanisms to suppress endotoxin-induced cytokine release.

Figure 6:
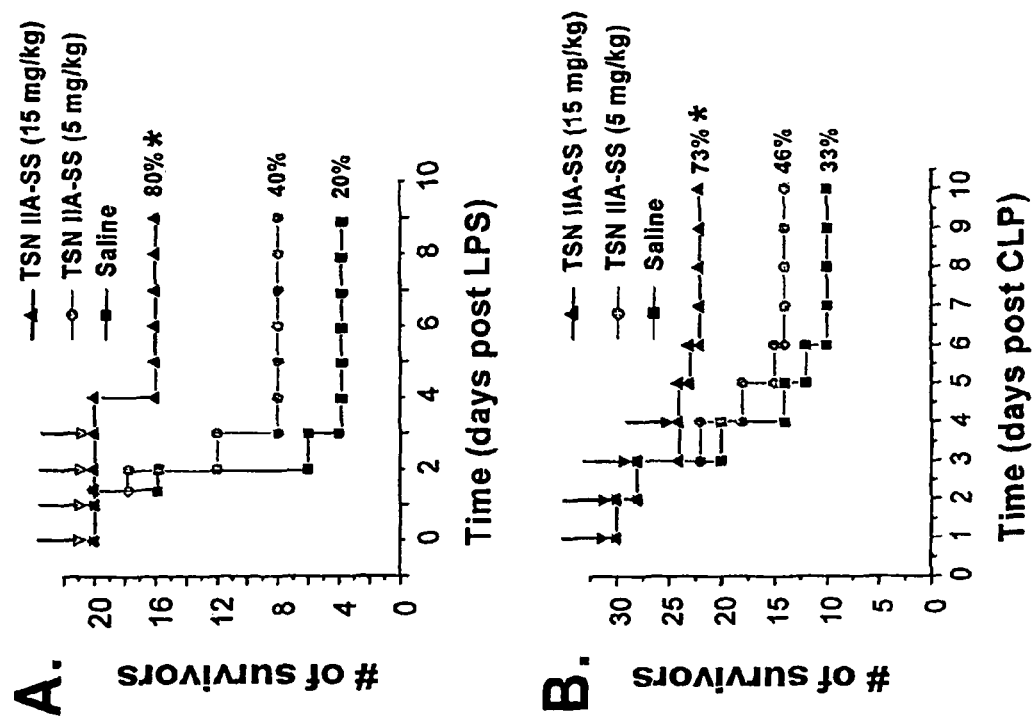
FIG. 6 is graphs showing that TSNIIA-SS dose-dependently protects mice against lethal endotoxemia (Panel A) and lethal sepsis (Panel B). Balb/C mice were subjected to lethal endotoxemia (LPS, 15 mg/kg, i.p.), or sepsis (induced by CLP). At +0.5, +24, +48, and +72 hours post the onset of endotoxemia, or +24, +48, +72, +96 hours post the onset of sepsis, animals were intraperitoneally administered with saline (0.2 ml/mouse), or TSNIIA-SS (0.2 ml/mouse, at indicated doses), and animal survival was monitored for up to two weeks. The Kaplan-Meier method was used to compare the differences in mortality rates between groups. *, P<0.05 versus saline.

TSNIIA-SS protects against lethal endotoxemia. In light of the capacity of TSNIIA-SS in attenuating LPS-induced HMGB1 release, its efficacy was evaluated in an animal model of lethal endotoxemia Administration of a single dose of TSNIIA-SS 30 minutes after an L.D.$_{75}$ dose of LPS did not significantly improve animal survival rate (25% for control receiving saline, n=20 mice/group; versus 37.5% for experimental group receiving TSNIIA-SS at 15 mg/kg, N=20 mice/group; P>0.05). By treating animals with three additional doses of TSNIIA-SS (+24, +48, and 72 hr), a dose-dependent improvement in animal survival was observed (from 20% to 80%, FIG. 6A). Furthermore, administration of TSNIIA-SS dose-dependently attenuated circulating HMGB1 levels (140±20 ng/ml, LPS+vehicle; versus 40±25 ng/ml; n=10, p<0.01), suggesting that TSNIIA-SS protects animals against lethal endotoxemia partly through attenuating systemic HMGB1 accumulation.

TSNIIA-SS rescues mice from lethal sepsis. Although endotoxemia is useful to investigate the complex cytokine cascades, more clinically relevant animal models are necessary to explore therapeutic agents for the treatment of human sepsis. One well-characterized, standardized animal model of sepsis is induced by CLP. In light of the late and prolonged kinetics of HMGB1 accumulation in experimental sepsis (Yang et al. 2004), it was reasoned that it might be possible to rescue mice from lethal sepsis even if TSNIIA-SS is administered after the onset of sepsis. The first dose of TSNIIA-SS was given 24 h after the onset of sepsis, a time point at which mice developed clear signs of sepsis (including lethargy, diarrhea, piloerection). Intraperitoneal administration with a single dose of TSNIIA-SS 24 h after the onset of sepsis failed to improve survival rate (33% for control receiving saline, n=24 mice/group; versus 50% for experimental group receiving TSNIIA-SS at 15 mg/kg, n=24 mice/group, P>0.05). However, repeated administration of TSNIIA-SS beginning twenty-four hours after the onset of sepsis (followed by additional doses at 48, 72, and 96 hours post sepsis) conferred a dose-dependent protection against lethal sepsis (N=30 mice per group, FIG. 6B), significantly increasing animal survival rate from 33% to 73% (P<0.05).

TSNIIA-SS attenuates sepsis-induced systemic HMGB1 accumulation and liver injury. To gain insight into its protective mechanism, the effects of TSNIIA-SS on the systemic accumulation of TNF, nitric oxide, and HMGB1 were evaluated. Consistent with early report (Villa et al. 1995), systemic TNF was barely detectable at late stage of sepsis. Delayed administration of TSNIIA-SS did not attenuate circulating TNF levels at 52 h after the onset of sepsis (TNF=65+15 ng/L, vehicle control group, N=10 mice/group; versus TNF=85+23 ng/L, TSNIIA-SS group, N=10 mice/group; P>0.05). Similarly, delayed administration of TSNIIA-SS did not attenuate circulating nitric oxide levels at 52 h after the onset of sepsis (18.0±4.5 µmol/L, vehicle control group; versus 15.5±3.3 µmol/L, TSNIIA-SS; n=3, P>0.05). In contrast, repeated administration of TNSIIA-SS dose-dependently, and significantly attenuated circulating HMGB1 levels in septic mice (FIG. 7A, P<0.05), indicating that TSNIIA-SS confers protection against lethal sepsis partly by attenuating systemic HMGB1 accumulation.

To determine if attenuation of systemic HMGB1 accumulation is accompanied by a protective effect against sepsis-induced tissue injury, necropsy was performed, where tissues were examined by histology at 48 hours post the onset of sepsis. Consistent with previous reports (Zhou et al. 1998), there were no noticeable histological changes in the heart, kidney, intestine, and brain (data not shown), confirming the notion that sepsis is not associated with any characteristic pathological changes in these tissues (Hotchkiss and Karl 2003). However, in agreement with previous reports (Ayala et al. 2000; Qin et al. 2006), foci of hepatic necrosis were noticed in 2 (out of 12) survivors of the control (saline) group (FIG. 7B). Notably, hepatic injury could not be evaluated in 3 (out of 15) animals of the control group that died early (3648 hours post CLP), and the exclusion of these 3 dead animals in the subsequent organ injury assessment may lead to an underestimation of TNSIIA-SS-mediated protective effects. In contrast, these signs of hepatic necrosis were not observed in any of the 15 survivors of the experimental group (TSNIIA-SS, 15 mg/kg, FIG. 7B).

TSNIIA-SS protects against sepsis-induced cardiac dysfunction. Since TSNIIA-SS has been successfully used for patients with cardiovascular disorders (Ji et al. 2000), we also evaluated whether or not it improves cardiovascular function in septic animals. Despite the lack of myocardial injury (Zhou et al. 1998), there is a hypodynamic change in cardiovascular function manifested by a significant decrease in cardiac output in the late stage (e.g., 20 h post the onset) of sepsis (Yang et al. 2002b). Administration of TSNIIA-SS did not significantly affect the mean arterial blood pressure (106.1±4.7 mm Hg, CLP group; versus 96.4±8.7 mm Hg; n=6, p>0.05), but slightly reduced the heart rate (378.3±25.1 beats/minutes, CLP group; versus 334.1±25.8 beats/minutes, CLP+TSNIIA-SS, 15 mg/kg, n=6, p<0.05). More importantly, it dose-dependently reduced total peripheral vascular resistance (FIG. 8A), and yet significantly increased cardiac stroke volume (FIG. 8B), and cardiac output (FIG. 8C). Taken together, these data indicate that TSNIIA-SS, an effective pharmacologic agent used for patients with cardiovascular disorders in China, appears to be protective against sepsis-induced cardiovascular dysfunction in an animal model of sepsis.

Discussion

The pathogenesis of lethal sepsis remains obscure, but is associated with dys-regulated inflammatory response, tissue injury, and multiple organ dys-function. The inflammatory response is mediated in part by bacterial endotoxin (Ayala et al. 2000), which stimulate macrophages/monocytes to sequentially release early (e.g., TNF and IL-1) and late (e.g., HMGB1) proinflammatory cytokines. Although early cytokines may be protective against infection (Eskandari et al. 1992), dys-regulated inflammatory response sustained by late-acting mediators (such as HMGB1) may contribute to the development of tissue injury, and organ dysfunction at late stage of lethal sepsis. Therefore, agents capable of selectively attenuating systemic HMGB1 accumulation may hold potential in the treatment of lethal sepsis.

Many non-steroidal anti-inflammatory drugs (NSAIDs, e.g., aspirin, ibuprofen, and indomethacin) fail to protect against lethal sepsis (Villa et al. 1995), and consistently fail to significantly inhibit LPS-induced HMGB1 release (Hasselgren et al. 1985; Noronha-Blob et al. 1993). On the other hand, the Chinese herb Danshen (Saliva miltiorrhizae), contains medicinal substances (such as tanshinone I, tanshinone IIA, and cryptotanshinone) that effectively attenuate endotoxin-induced HMGB1 release in macrophage/monocyte cultures. However, due to poor solubility and bioavailability, tanshinone I and tanshinone IIA failed to rescue mice from lethal sepsis, even after repeated administration at 24, 48, 72, and 96 hours post the onset of sepsis (survival rate=50%, control vehicle group; versus survival rate=57%, TSN I group, 12 mg/kg; survival rate=61%, TSN IIA group, 12 mg/kg; N=14 mice/group, p>0.05), forcing us to explore other water-soluble derivatives as potential therapeutic agents.

TSNIIA-SS, a clinically approved drug for patients with cardiovascular disorders, completely abrogates endotoxin-induced HMGB1 release in macrophage/monocyte cultures. The mechanism by which TSNIIA-SS inhibits endotoxin-induced HMGB1 release remains elusive, but is partly attributable to its ability to interfere with LPS-induced HMGB1 cytoplasmic translocation. Although containing a similar backbone chemical structure as glucocorticoids, TSNIIA-SS does not appear to use the glucocorticoid receptor to inhibit HMGB1 release, because the specific glucocorticoid receptor antagonist RU486 fails to abolish TSNIIA-SS-mediated inhibition of HMGB1 release. Interestingly, tanshinone I can inhibit phospholipase A2 (Kim et al. 2002), an enzyme that enhances endotoxin-induced HMGB1 release by generating lysophosphatidylcholine (Chen et al. 2005). Similarly, cryptotanshinone can inhibit acetylcholinesterase (Gardella et al. 2002), an enzyme that eliminates the HMGB-1-inhibiting neurotransmitter, acetylcholine (Borovikova et al. 2000; Ren et al. 2004; Wang et al. 2004b). It will thus be important to determine whether TSNIIA-SS inhibits HMGB1 release by inhibiting sPLA2 or acetylcholinesterase in future studies.

At concentrations that completely abrogates LPS-induced HMGB1 release, TSNIIA-SS does not affect the release of most (58 out of 62) other cytokines, indicating selectivity for inhibiting HMGB1 over most other cytokines. Even when given several hours after LPS stimulation, TSNIIA-SS is still effective in blocking HMGB1 release, distinguishing itself from all previously known HMGB1 inhibitors (including ethyl pyruvate, nicotine, and stearoyl lysophosphatidylcholine) (Chen et al. 2005; Ulloa et al. 2002; Wang et al. 2004b). These unique properties enable us to strategically administer TSNIIA-SS in a delayed fashion to selectively attenuate systemic HMGB1 accumulation at late stage of sepsis. Indeed, delayed administration of TSNIIA-SS beginning at 24 h after CLP, a time point when all mice developed clear signs of sepsis (and some mice started to die), significantly rescued mice from lethal sepsis.

The observations that TSNIIA-SS failed to attenuate systemic nitric oxide accumulation, and failed to increase the mean arterial pressure at late stage of sepsis, argue against a nitric oxide-dependent protective mechanism. Although TSNIIA-SS can somewhat reduce LPS-induced TNF secretion in monocytes (but not macrophages), its TNF-suppression activity may not account for its protective effects against lethal sepsis. First, TNF accumulates systemically within few hours following CLP (Villa et al. 1995), long before our strategic, delayed administration of TSNIIA-SS (at 24 h post CLP). Consistently, we observed that delayed administration of TSNIIA-SS did not significantly attenuate systemic accumulation of TNF at late stage of sepsis. Second, TNF may play a protective role in sepsis, because suppression of TNF activities with neutralizing antibodies did not improve, but actually worsen survival in animal model of sepsis (Eskandari et al. 1992). It remains to be determined, however, whether the TNF-suppression activity of TSNIIA-SS is attributable to its protective effects against lethal endotoxemia.

In sharp contrast, delayed administration of TSNIIA-SS significantly attenuates systemic HMGB1 accumulation, suggesting that TSNIIA-SS rescues mice from lethal sepsis partly through attenuation of systemic accumulation of late-acting proinflammatory mediators. Nevertheless, the present study cannot eliminate the possibility that TSNIIA-SS confers protection against lethal endotoxemia or sepsis through additional mechanisms (such as inhibition of HMGB1-mediated inflammatory response). Indeed, our preliminary experimental data indicated that TNSIIA-SS, at concentrations up to 100 µM, effectively attenuates HMGB1-induced release of TNF (by 50-60%) and nitric oxide (by 90-95%) in murine macrophage cultures, implicating that TSNIIA-SS may improve animal survival by suppressing HMGB1 release and cytokine activities.

Repeated administration of TSNIIA-SS abrogates the development of hepatic injury at late stage of sepsis. Notably, assessment of organ injury, which occurs predominantly at a late (rather than early) stage of sepsis, is unquestionably problematic. For instance, hepatic injury could not be evaluated in 3 (out of 15) animals that died early (36-48 hours post CLP), although these animals might similarly suffer from hepatic injury prior to death. Consequently, the exclusion of dead animals in the subsequent organ injury assessment may have led to an underestimation of TNSIIA-SS-mediated protection against hepatic injury, particularly in light of the observation that HMGB1-specific monoclonal antibodies similarly ameliorate hepatic injury (Qin et al. 2006).

In response to septic insult, rodents develop an early, hyperdynamic cardiovascular response characterized by an increase in cardiac output and a decrease in total peripheral resistance 5 h post CLP, which is followed by a late, hypodynamic cardiovascular response manifested by a decrease in cardiac output and an increase in total peripheral resistance at 20-24 h post CLP (Yang et al. 2002a). As an effective pharmacologic agent used for patients with cardiovascular disorders in China, TSNIIA-SS dramatically reduces total peripheral vascular resistance, but significantly increases cardiac stroke volume and cardiac output in septic animals. Clinically, some patients with severe sepsis have normal or high cardiac output, which fuels an ongoing debate regarding the necessity to raise cardiac output (to improve oxygen delivery) and reduce systemic vascular resistance (to improve tissue oxygenation) for patients with severe sepsis (Sharma and Dellinger 2003; Vincent 2003).

References

Abraham, E., J. Arcaroli, A. Carmody, H. Wang, and K. J. Tracey. 2000. "HMG-1 as a mediator of acute lung inflammation." J Immunol. 165:2950-2954.

Andersson, U., H. Wang, K. Palmblad, A. C. Aveberger, O. Bloom, H. Erlandsson-Harris, A. Janson, R. Kokkola, M. Zhang, H. Yang, and K. J. Tracey. 2000. "High Mobility Group 1 Protein (HMG-1) Stimulates Proinflammatory Cytokine Synthesis in Human Monocytes." J Exp Med. 192:565-570.

Ayala, A., G. Y. Song, C. S. Chung, K. M. Redmond, and I. H. Chaudry. 2000. "Immune depression in polymicrobial sepsis: the role of necrotic (injured) tissue and endotoxin." Crit. Care Med. 28:2949-2955.

Bernard, G. R., J. L. Vincent, P. F. Laterre, S. P. LaRosa, J. F. Dhainaut, A. Lopez-Rodriguez, J. S. Steingrub, G. E. Garber, J. D. Helterbrand, E. W. Ely, and C. J. J. Fisher. 2001. "Efficacy and safety of recombinant human activated protein C for severe sepsis." N Engl J Med. 344:699-709.

Borovikova, L. V., S. Ivanova, M. Zhang, H. Yang, G. I. Botchkina, L. R. Watkins, H. Wang, N. Abumrad, J. W.

Eaton, and K. J. Tracey. 2000. "Vagus nerve stimulation attenuates the systemic inflammatory response to endotoxin." Nature. 405:458-462.

Calandra, T., B. Echtenacher, D. L. Roy, J. Pugin, C. N. Metz, L. Hultner, D. Heumann, D. Mannel, R. Bucala, and M. P. Glauser. 2000. "Protection from septic shock by neutralization of macrophage migration inhibitory factor." Nat Med. 6:164-170.

Chacur, M., E. D. Milligan, L. S. Gazda, C. Armstrong, H. Wang, K. J. Tracey, S. F. Maier, and L. R. Watkins. 2001. "A new model of sciatic inflammatory neuritis (SIN): induction of unilateral and bilateral mechanical allodynia following acute unilateral peri-sciatic immune activation in rats." Pain. 94:231-244.

Chang, D. M., S. Y. Kuo, J. H. Lai, and M. L. Chang. 1999. "Effects of anti-rheumatic herbal medicines on cellular adhesion molecules." Ann Rheum Dis. 58:366-371.

Chen, G., J. Li, M. Ochani, B. Rendon-Mitchell, X. Qiang, S. Susarla, L. Ulloa, H. Yang, S. Fan, S. M. Goyert, P. Wang, K. J. Tracey, A. E. Sama, and H. Wang. 2004. "Bacterial endotoxin stimulates macrophages to release HMGB1 partly through CD14- and TNF-dependent mechanisms." J Leukoc. Biol. 76:994-1001.

Chen, G., J. Li, X. Qiang, C. J. Czura, M. Ochani, K. Ochani, L. Ulloa, H. Yang, K. J. Tracey, P. Wang, A. E. Sama, and H. Wang. 2005. "Suppression of HMGB1 release by stearoyl lysophosphatidylcholine: an additional mechanism for its therapeutic effects in experimental sepsis." J. Lipid Res. 46:623-627.

Dai, Y., K. Miki, T. Fukuoka, A. Tokunaga, T. Tachibana, E. Kondo, and K. Noguchi. 2000. "Suppression of neuropeptides' mRNA expression by herbal medicines in a rat model of peripheral inflammation." Life Sci. 66:19-29.

Dinarello, C. A. and R. C. Thompson. 1991. "Blocking IL-1: interleukin 1 receptor antagonist in vivo and in vitro." Immunol Today. 12:404-410.

Dinapoli, M. R., C. L. Calderon, and D. M. Lopez 1996. "The altered tumoricidal capacity of macrophages isolated from tumor-bearing mice is related to reduce expression of the inducible nitric oxide synthase gene." J Exp Med. 183: 1323-1329.

Eskandari, M. K., G. Bolgos, C. Miller, D. T. Nguyen, L. E. DeForge, and D. G. Remick. 1992. "Anti-tumor necrosis factor antibody therapy fails to prevent lethality after cecal ligation and puncture or endotoxemia" J Immunol. 148: 2724-2730.

Fink, M. P. 1993. "Adoptive immunotherapy of gram-negative sepsis: use of monoclonal antibodies to lipopolysaccharide." Crit Care Med. 21:S32-S39.

Gardella, S., C. Andrei, D. Ferrera, L. V. Lotti, M. R. Torrisi, M. E. Bianchi, and A. Rubartelli. 2002. "The nuclear protein HMGB1 is secreted by monocytes via a non-classical, vesicle-mediated secretory pathway." EMBO Rep. 3:955-1001.

Hasselgren, P. O., M. Talamini, R. LaFrance, J. H. James, J. C. Peters, and J. E. Fischer. 1985. "Effect of indomethacin on proteolysis in septic muscle." Ann. Surg. 202:557-562.

Heinzel, F. P. 1990. "The role of IFN-gamma in the pathology of experimental endotoxemia." J Immunol. 145:2920-2924.

Hotchkiss, R. S., K. W. Tinsley, P. E. Swanson, K. C. Chang, J. P. Cobb, T. G. Buchman, S. J. Korsmeyer, and I. E. Karl. 1999. "Prevention of lymphocyte cell death in sepsis improves survival in mice." Proc. Natl. Acad. Sci. U.S.A. 96:14541-14546.

Hotchkiss, R. S. and I. E. Karl. 2003. "The pathophysiology and treatment of sepsis." N Engl J Med. 348:138-150.

Jang, S. I., S. I. Jeong, K. J. Kim, H. J. Kim, H. H. Yu, R. Park, H. M. Kim, and Y. O. You. 2003. "Tanshinone IIA from *Salvia miltiorrhiza* inhibits inducible nitric oxide synthase expression and production of TNF-α, IL-1β and IL-6 in activated RAW 264.7 cells." Planta Med. 69:1057-1059.

Ji, X. Y., B. K. Tan, and Y. Z. Zhu. 2000. "*Salvia miltiorrhiza* and ischemic diseases." Acta Pharmacol. Sin. 21:1089-1094.

Joe, S. M., I. S. Lee, Y. T. Lee, J. H. Lee, and B. T. Choi. 2001. "Suppression of collagen-induced arthritis in rats by continuous administration of dae-bang-poong-tang (da-fang-feng-tang)." Am J Chin. Med. 29:355-365.

Kang, B. Y., S. W. Chung, S. H. Kim, S. Y. Ryu, and T. S. Kim. 2000. "Inhibition of interleukin-12 and interferon-gamma production in immune cells by tanshinones from *Salvia miltiorrhiza*." Immunopharmacology. 49:355-361.

Kim, S. Y., T. C. Moon, H. W. Chang, K. H. Son, S. S. Kang, and H. P. Kim. 2002. "Effects of tanshinone I isolated from *Salvia miltiorrhiza* bunge on arachidonic acid metabolism and in vivo inflammatory responses." Phytother. Res. 16:616-620.

Li, X. H. and R. Y. Tang. 1991. "[Relationship between inhibitory action of tanshinone on neutrophil function and its prophylactic effects on myocardial infarction]." Zhongguo Yao Li Xue. Bao. 12:269-272.

Lin, C. C., C. H. Lin, H. F. Chiu, and M. F. Hu. 1992. "The pharmacological and pathological studies on Taiwan folk medicine (VII): The anti-inflammatory effect of Echinops grjiisii." Am J Chin. Med. 20:127-134.

Llewelyn, M. and J. Cohen. "New insights into the pathogenesis and therapy of sepsis and septic shock." Curr Clin Top. Infect Dis 2001; 21:148-71. 21:148-71:148-171.

Miyamoto, K., K. Furusawa, A. Kuroiwa, M. Saito, T. Miyata, and T. Furukawa. 1990. "Effects of qing-fei-tang on the airway inflammation and clearance." Am J Chin. Med. 18:5-18.

Noronha-Blob, L., V. C. Lowe, L. Otterbein, L. Steranka, and R. M. Burch. 1993. "NPC 15669 reduces mortality associated with sepsis in rats." J Pharmacol Exp. Ther. 267:664-669.

O'Connor, K. A., M. K. Hansen, P. C. Rachal, M. M. Deak, J. C. Biedenkapp, E. D. Milligan, J. D. Johnson, H. Wang, S. F. Maier, K. J. Tracey, and L. R. Watkins. 2003. "Further characterization of high mobility group box 1 (HMGB1) as a proinflammatory cytokine: central nervous system effects." Cytokine. 24:254-265.

Paludan, S. R. 1998. "Interleukin-4 and interferon-gamma: the quintessence of a mutual antagonistic relationship." Scand J Immunol. 48:459-468.

Park, J. S., J. Arcaroli, H. K. Yum, H. Yang, H. Wang, K. Y. Yang, K. H. Choe, D. Strassheim, T. M. Pitts, K. J. Tracey, and E. Abraham. 2003. "Activation of gene expression in human neutrophils by high mobility group box 1 protein." Am J Physiol Cell Physiol. 284:C870-C879.

Qin, S., H. Wang, R. Yuan, H. Li, M. Ochani, K. Ochani, M. Rosas-Ballina, C. J. Czura, J. M. Huston, E. Miller, X. Lin, B. Sherry, A. Kumar, G. Larosa, W. Newman, K. J. Tracey, and H. Yang. 2006. "Role of HMGB1 in apoptosis-mediated sepsis lethality." J Exp. Med. 203:1637-1642.

Ren, Y., P. J. Houghton, R. C. Hider, and M. J. Howes. 2004. "Novel diterpenoid acetylcholinesterase inhibitors from *Salvia miltiorrhiza*." Planta Med. 70:201-204.

Rendon-Mitchell, B., M. Ochani, J. Li, J. Han, H. Wang, H. Yang, S. Susarla, C. Czura, R. A. Mitchell, G. Chen, A. E. Sama, K. J. Tracey, and H. Wang. 2003. "IFN-gamma Induces High Mobility Group Box 1 Protein Release Partly Through a TNF-Dependent Mechanism." J Immunol. 170: 3890-3897.

Riedemann, N. C., R. F. Guo, and P. A. Ward. 2003a. "The enigma of sepsis." J Clin Invest. 112:460-467.

Riedemann, N. C., R. F. Guo, and P. A. Ward. 2003b. "Novel strategies for the treatment of sepsis." Nat. Med. 9:517-524.

Sappington, P. L., R. Yang, H. Yang, Tracey K. J., R. L. Delude, and M. P. Fink. 2002. "HMGB1 B box increases the permeability of Caco-2 enterocytic monolayers and causes derangements in intestinal barrier function in mice." Gastroenterology. 123:790-802.

Scaffidi, P., T. Misteli, and M. E. Bianchi. 2002. "Release of chromatin protein HMGB1 by necrotic cells triggers inflammation." Nature. 418:191-195.

Shanghai Cooperative Group for the Study of Tanshinone IIA. 1984. "Therapeutic effect of sodium tanshinone IIA sulfonate in patients with coronary heart disease." J. Tradit. Chin Med. 4:20-24.

Sharma, V. K. and R. P. Dellinger. 2003. "The International Sepsis Forum's frontiers in sepsis: High cardiac output should not be maintained in severe sepsis." Crit Care. 7:272-275.

Shen, T. Y., S. B. Hwang, M. N. Chang, T. W. Doebber, M. H. Lam, M. S. Wu, X. Wang, G. Q. Han, and R. Z. Li. 1985. "Characterization of a platelet-activating factor receptor antagonist isolated from haifenteng (*Piper futokadsura*): specific inhibition of in vitro and in vivo platelet-activating factor-induced effects." Proc Natl Acad Sci USA. 82:672-676.

Shilin, H. et al. 1987. "Experimental studies on the anti-endotoxin-shock effect of Tadix salviae miltiorrhizae composite." J. Trad. Chin. Med. 7:131-134.

Takahashi, K., X. Ouyang, K. Komatsu, N. Nakamura, M. Hattori, A. Baba, and J. Azuma. 2002. "Sodium tanshinone IIA sulfonate derived from Danshen (*Salvia miltiorrhiza*) attenuates hypertrophy induced by angiotensin II in cultured neonatal rat cardiac cells." Biochem. Pharmacol. 64:745-749.

Tang, D., Y. Shi, R. Kang, T. Li, W. Xiao, H. Wang, and X. Xiao. 2006. "Hydrogen peroxide stimulates macrophages and monocytes to actively release HMGB1." J Leukoc. Biol. (Epub).

Tao, X., L. Ma, Y. Mao, and P. E. Lipsky. 1999. "Suppression of carrageenan-induced inflammation in vivo by an extract of the Chinese herbal remedy *Tripterygium wilfordii* Hook F." Inflamm Res. 48:139-148.

Tracey, K. J., Y. Fong, D. G. Hesse, K. R. Manogue, A. T. Lee, G. C. Kuo, S. F. Lowry, and A. Cerami. 1987. "Anti-cachectin/TNF monoclonal antibodies prevent septic shock during lethal bacteraemia." Nature. 330:662-664.

Ueno, H., T. Matsuda, S. Hashimoto, F. Amaya, Y. Kitamura, M. Tanaka, A. Kobayashi, I. Maruyama, S. Yamada, N. Hasegawa, J. Soejima, H. Koh, and A. Ishizaka 2004. "Contributions of high mobility group box protein in experimental and clinical acute lung injury." Am. J. Respir. Crit. Care Med. 170:1310-1316.

Ulloa, L., M. Ochani, H. Yang, M. Tanovic, D. Halperin, R. Yang, C. J. Czura, M. P. Fink, and K. J. Tracey. 2002. "Ethyl pyruvate prevents lethality in mice with established lethal sepsis and systemic inflammation." Proc Natl Acad Sci USA. 99:12351-12356.

Villa, P., G. Sartor, M. Angelini, M. Sironi, M. Conni, P. Gnocchi, A. M. Isetta, G. Grau, W. Buurman, L. J. van Tits, and 1995. "Pattern of cytokines and pharmacomodulation in sepsis induced by cecal ligation and puncture compared with that induced by endotoxin." Clin. Diagn. Lab Immunol. 2:549-553.

Vincent, J. L. 2003. "The International Sepsis Forum's frontiers in sepsis: High cardiac output should be maintained in severe sepsis." Crit Care. 7:276-278.

Waage, A., G. Slupphaug, and R. Shalaby. 1990. "Glucocorticoids inhibit the production of IL6 from monocytes, endothelial cells and fibroblasts." Eur. J Immunol. 20:2439-2443.

Wang, H., C. J. Czura, and K. J. Tracey. 2004a. "Lipid unites disparate syndromes of sepsis." Nat. Med. 10:124-125.

Wang, C. C., J. E. Lai, L. G. Chen, K. Y. Yen, and L. L. Yang. 2000. "Inducible nitric oxide synthase inhibitors of Chinese herbs. Part 2: naturally occurring furanocoumarins." Bioorg. Med. Chem. 8:2701-2707.

Wang, H., D. C. Harrison-Shostak, J. J. Lemasters, and B. Herman. 1996. "Contribution of pH-dependent group II phospholipase A2 to chemical hypoxic injury in rat hepatocytes." FASEB J. 10:1319-1325.

Wang, H., M. Zhang, M. Bianchi, B. Sherry, A. Sama, and K. J. Tracey. 1998. "Fetuin (alpha2-HS-glycoprotein) opsonizes cationic macrophage deactivating molecules." Proc Natl Acad Sci USA. 95:14429-14434.

Wang, H., O. Bloom, M. Zhang, J. M. Vishnubhakat, M. Ombrellino, J. Che, A. Frazier, H. Yang, S. Ivanova, L. Borovikova, K. R. Manogue, E. Faist, E. Abraham, J. Andersson, U. Andersson, P. E. Molina, N. N. Abumrad, A. Sama, and K. J. Tracey. 1999. "HMG-1 as a late mediator of endotoxin lethality in mice." Science. 285:248-251.

Wang, H., H. Yang, C. J. Czura, A. E. Sama, and K. J. Tracey. 2001. "HMGB1 as a Late Mediator of Lethal Systemic Inflammation." Am J Respir Crit Care Med. 164:1768-1773.

Wang, H., C. J. Czura, and K. J. Tracey. 2004a. "Lipid unites disparate syndromes of sepsis." Nat. Med. 10:124-125.

Wang, H., H. Liao, M. Ochani, M. Justiniani, X. Lin, L. Yang, Y. Al Abed, H. Wang, C. Metz, E. J. Miller, K. J. Tracey, and L. Ulloa. 2004b. "Cholinergic agonists inhibit HMGB1 release and improve survival in experimental sepsis." Nat. Med. 10: 1216-1221.

Wang, H., H. Yang, and K. J. Tracey. 2004c. "Extracellular role of HMGB1 in inflammation and sepsis." J Intern. Med. 255:320-331.

Wang, H. et al. 2006. "The Aqueous Extract of a Popular Herbal Nutrient Supplement, *Angelica sinensis*, protects mice against lethal endotoxemia and sepsis." J. Nutr. 136: 1-6 (In Press).

Wei, F., S. Zou, A. Young, R. Dubner, and K. Ren. 1999. "Effects of four herbal extracts on adjuvant-induced inflammation and hyperalgesia in rats." J Altern. Complement Med. 5:429-436.

Wu, T. W., L. H. Zeng, K. P. Fung, J. Wu, H. Pang, A. A. Grey, R. D. Weisel, and J. Y. Wang. 1993. "Effect of sodium tanshinone IIA sulfonate in the rabbit myocardium and on human cardiomyocytes and vascular endothelial cells." Biochem. Pharmacol. 46:2327-2332.

Yagi, A., N. Okamura, K. Tanonaka, and S. Takeo. 1994. "Effects of tanshinone VI derivatives on post-hypoxic contractile dysfunction of perfused rat hearts." Planta Med. 60:405-409.

Yang, H., M. Ochani, J. Li, X. Qiang, M. Tanovic, H. E. Harris, S. M. Susarla, L. Ulloa, H. Wang, R. DiRaimo, C. J. Czura, H. Wang, J. Roth, H. S. Warren, M. P. Fink, M. J. Fenton, U. Andersson, and K. J. Tracey. 2004. "Reversing established sepsis with antagonists of endogenous high-mobility group box 1." Proc Natl Acad Sci USA. 101:296-301.

Yang, S., C. S. Chung, A. Ayala, I. H. Chaudry, and P. Wang. 2002a "Differential alterations in cardiovascular responses during the progression of polymicrobial sepsis in the mouse." Shock. 17:55-60.

Yang, S., M. Zhou, I. H. Chaudry, and P. Wang. 2002b. "Novel approach to prevent the transition from the hyperdynamic phase to the hypodynamic phase of sepsis: role of adrenomedullin and adrenomedullin binding protein-1." Ann. Surg. 236:625-633.

Zhou, M., P. Wang, and I. H. Chaudry. 1998. "Cardiac contractility and structure are not significantly compromised even during the late, hypodynamic stage of sepsis." Shock. 9:352-358.

Zhang, M., T Caragine, H Wang, P S Cohen, G Botchkina, K Soda, M Bianchi, P Ulrich, A Cerami, B Sherry, K J Tracey. 1997. "Spermine inhibits proinflammatory cytokine synthesis in human mononuclear cells: a counterregulatory mechanism that restrains the immune response." J Exp Med 185:1759-1768.

Zhou, G. Y., B. L. Zhao, J. W. Hou, G. E. Ma, and W. J. Xin. 1999. "Protective effects of sodium tanshinone IIA sulphonate against adriamycin-induced lipid peroxidation in mice hearts in vivo and in vitro." Pharmacol. Res. 40:487-491.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating a mammal at risk for or having sepsis, septicemia, and/or endotoxic shock, the method comprising administering to the mammal a purified tanshinone in a manner effective to reduce or prevent a physiologic effect of the sepsis, septicemia, and/or endotoxic shock, wherein the purified tanshinone is tanshinone IIA sodium sulfonate.

2. The method of claim 1, wherein the mammal is a human.

3. The method of claim 1, for treating a mammal at risk for sepsis.

4. The method of claim 1, for treating a mammal at risk for septicemia.

5. The method of claim 1, for treating a mammal at risk for endotoxic shock.

6. The method of claim 1, for treating a mammal having sepsis.

7. The method of claim 1, for treating a mammal having septicemia.

8. The method of claim 1, for treating a mammal having endotoxic shock.

* * * * *